(12) United States Patent
Yamasaki et al.

(10) Patent No.: US 7,752,007 B2
(45) Date of Patent: Jul. 6, 2010

(54) SETTING INFORMATION MANAGEMENT SYSTEM, SETTING INFORMATION MANAGEMENT DEVICE, SETTING INFORMATION MANAGEMENT METHOD, AND COMPUTER PROGRAM PRODUCT

(75) Inventors: Hirokazu Yamasaki, Kobe (JP); Takashi Matsuzawa, Kakogawa (JP)

(73) Assignee: Sysmex Corporation, Kobe (JP)

( * ) Notice: Subject to any disclaimer, the term of this patent is extended or adjusted under 35 U.S.C. 154(b) by 141 days.

(21) Appl. No.: 12/079,807

(22) Filed: Mar. 28, 2008

(65) Prior Publication Data

US 2008/0262776 A1 Oct. 23, 2008

(30) Foreign Application Priority Data

Mar. 30, 2007 (JP) .............................. 2007-093060

(51) Int. Cl.
*G06F 19/00* (2006.01)
(52) U.S. Cl. ..................... 702/127; 702/108; 707/10; 422/58; 422/65; 422/67; 422/68.1; 422/102; 700/209
(58) Field of Classification Search ................. 702/127, 702/182, 183, 184, 185, 187, 108; 707/10; 422/58, 68.1, 65, 67, 102; 700/209
See application file for complete search history.

(56) References Cited

U.S. PATENT DOCUMENTS

| | | | | |
|---|---|---|---|---|
| 4,855,110 A | * | 8/1989 | Marker et al. ............... 422/102 |
| 5,209,903 A | * | 5/1993 | Kanamori et al. ............. 422/65 |
| 6,019,945 A | * | 2/2000 | Ohishi et al. .................. 422/65 |
| 6,532,535 B1 | * | 3/2003 | Maffezzoni et al. ............ 713/1 |
| 6,629,060 B2 | * | 9/2003 | Okuno et al. ................ 702/187 |
| 7,400,983 B2 | * | 7/2008 | Feingold et al. ............... 702/31 |
| 2001/0051952 A1 | * | 12/2001 | Nakazato ................. 707/104.1 |
| 2002/0016683 A1 | * | 2/2002 | Shiba et al. .................... 702/22 |
| 2003/0083774 A1 | * | 5/2003 | Simon et al. ................. 700/209 |
| 2004/0078641 A1 | * | 4/2004 | Fleischmann .................. 714/6 |
| 2005/0036912 A1 | * | 2/2005 | Yamakawa et al. ............ 422/65 |
| 2005/0111352 A1 | * | 5/2005 | Ho et al. ...................... 370/219 |
| 2005/0154734 A1 | * | 7/2005 | Zucchini ........................ 707/10 |
| 2006/0230393 A1 | * | 10/2006 | Doh et al. .................... 717/137 |
| 2007/0166195 A1 | * | 7/2007 | Padmanabhan et al. ..... 422/68.1 |
| 2007/0166196 A1 | * | 7/2007 | Bardell et al. ............... 422/68.1 |
| 2007/0172388 A1 | * | 7/2007 | Padmanabhan et al. ....... 422/58 |
| 2008/0240984 A1 | * | 10/2008 | Wakamiya et al. ............ 422/67 |

* cited by examiner

*Primary Examiner*—Carol S Tsai
(74) *Attorney, Agent, or Firm*—Brinks Hofer Gilson & Lione

(57) ABSTRACT

A setting information management method executed by a backup program stored in a portable storage medium by a processing computer of an analyzer, comprising: determining a type of the analyzer in which the backup program is executed from a plurality of types of analyzers; acquiring setting information of a program introduced to the processing computer based on the determination result; and storing the acquired setting information in the portable storage medium. A setting information management system, a setting information management device, and a computer program product is also disclosed.

20 Claims, 18 Drawing Sheets

FIG.14

| | FILE NAME | PROGRAM NAME | DIRECTORY | OUTLINE OF FILE | DETAILS |
|---|---|---|---|---|---|
| (a) | IPCONFIG.DOC | WINDOWS(R) | C | IP ADDRESS AND DEFAULT GATEWAY, ETC. | IP ADDRESS DEFAULT GATEWAY, DNS, COMPUTER NAME |
| (b) | REMOTE.+++ | REMOTE PROGRAM | C:¥PROGRAM FILES¥XXX | SETTING VALUE OF REMOTE OPERATION SOFTWARE | NICKNAME OF FACILITY, VARIOUS CONNECTION SETTINGS |
| (c) | a¥**.INI | XE PROGRAM | C:¥*** | SETTING VALUE OF NETWORK TRANSMISSION PROGRAM | NETWORK FACILITY ID, DEVICE SERIAL, DEVICE PRODUCT CODE ETC. |
| (c) | b****.INI | XE PROGRAM | C:¥***** | SETTING VALUE OF NETWORK TRANSMISSON PROGRAM | ON-LINE QC, PRESENCE OF EXECUTION OF REMOTE MAINTENANCE |
| d | c****.INI | XE PROGRAM | C:¥***** | SETTING VALUE OF XE-***** PROGRAM | VARIOUS SET VALUES OF XE-***** (MAINLY USER SETTING) |
| d | d****.INI | XE PROGRAM | C:¥***** | SETTING VALUE OF XE-***** PROGRAM | SET VALUE OF PRINTER |
| | ...... | ...... | ...... | ...... | ...... |

| Windows(R) NT IP Configuration | |
|---|---|
| Host Name | ipu |
| DNS Serrvers | 192.168.28.1 |
| Node Type | Broadcast |
| NetBIOS Scope ID | |
| IP Routing Enabled | No |
| WINS Proxy Enabled | No |
| Net BIOS Resolution DNS | No |
| Ethernet adapter ****** | |
| Description | ○○○ Ethernet Adapter |
| Physical Adress | ----- |
| DHCP Enabled | No |
| IP Adress | 192.168.28.142 |
| Subnet Mask | 255.255.255.0 |
| Default Gateway | 192.168.28.1 |

FIG.15

FIG.17
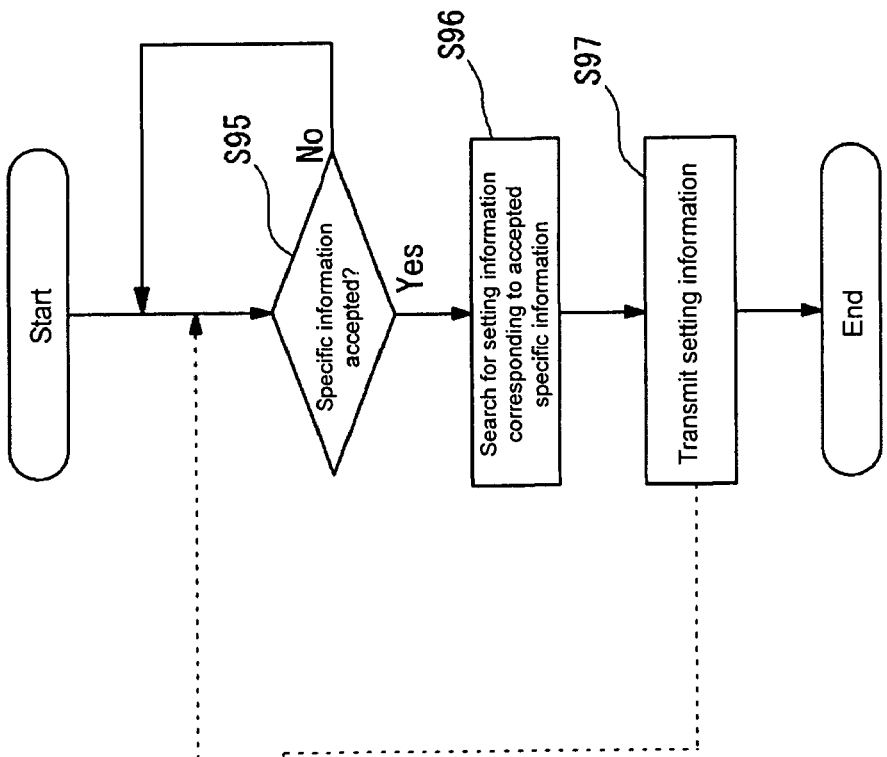
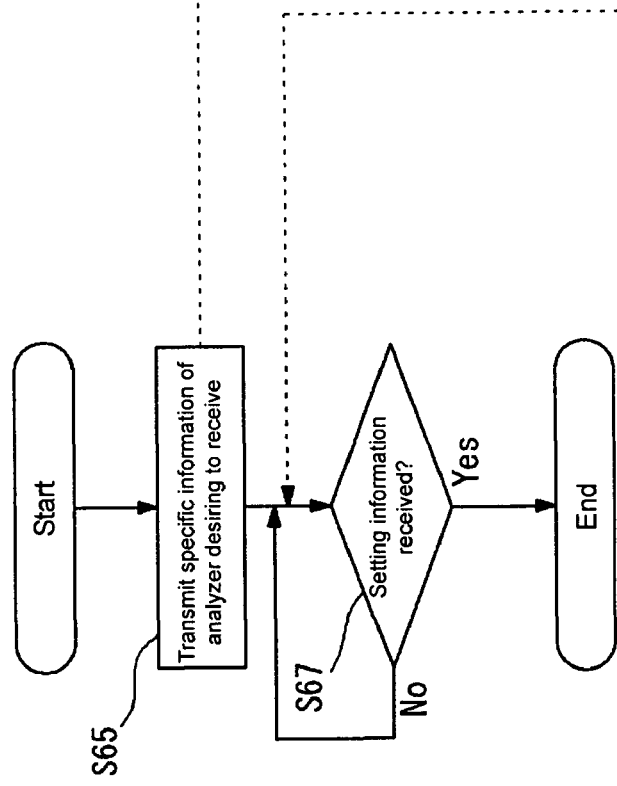

SETTING INFORMATION MANAGEMENT SYSTEM, SETTING INFORMATION MANAGEMENT DEVICE, SETTING INFORMATION MANAGEMENT METHOD, AND COMPUTER PROGRAM PRODUCT

RELATED APPLICATIONS

This application claims priority under 35 U.S.C. §119 to Japanese Patent Application Nos. 2007-093060 filed Mar. 30, 2007, the entire contents of which are hereby incorporated by reference.

FIELD OF INVENTION

The present invention relates to a setting information management system capable of acquiring, managing, and restoring setting information with respect to sample analyzers such as blood analyzer and urine particle analyzer, setting information management device, a setting information management method, and a computer program product.

BACKGROUND

Recently, an analyzer using blood, urine, and the like as a sample is generally configured by a measurement unit for measuring the sample, and a processing computer for processing the data of a measurement result output by the measurement unit. In such analyzer, the processing computer must be initialized or replaced if the processing computer malfunctions or fails. In this case, the technician that performs the maintenance re-installs a measurement data processing program of the analyzer, OS (Operating System), and the like from a recovery CD etc. to the processing computer and sets the environment of each program to recover the processing computer.

U.S. Patent Application Publication No. 2001-51952 discloses a technique of arranging a backup means for backing up registration information in the device and a recovery means for recovering the same in an analyzer of the sample, and physically dividing a hard disc for storing the registration information and a hard disc for storing backup information (backed up registration information).

In the analyzer disclosed in U.S. Patent Application Publication No. 2001-51952, the backup means and the recovery means are arranged in the analyzer and backup and restore of the data in the analyzer are executed using such means. A configuration of performing backup and restore of data of another analyzer using the backup means and the restore means arranged in the analyzer is not disclosed in U.S. Patent Application Publication No. 2001-51952. However, the technicians must normally handle various models of analyzers, and it is necessary to perform backup and restore of data for each model. Therefore, in the conventional technique, a dedicated backup program and a restore program needs to be created for every model of analyzer, whereby the cost and the man hour for creating the program increase.

Furthermore, in the analyzer disclosed in U.S. Patent Application Publication No. 2001-51952, the hard disc for data backup is arranged in the analyzer, and thus the user of the analyzer must manage the backup data. The backup data for each of a plurality of analyzers must be individually managed, which is a great burden on the user.

BRIEF SUMMARY

The scope of the present invention is defined solely by the appended claims, and is not affected to any degree by the statements within this summary.

A first aspect of the present invention is a setting information management system comprising: a plurality of types of analyzers comprising a measurement unit for measuring a sample and outputting measurement result data, and a processing computer for processing the measurement result data output from the measurement unit; and a computer readable portable storage medium storing a backup program; wherein the backup program is configured to cause the processing computer to function as, determining means for determining the type of the analyzer when the backup program is executed by the processing computer of the analyzer, setting information acquiring means for acquiring setting information of a program introduced to the processing computer of the analyzer from the processing computer based on a determination result of the determining means, and storage means for storing the setting information acquired by the setting information acquiring means in the storage medium.

A second aspect of the present invention is a setting information management system comprising: a plurality of analyzers comprising a measurement unit for measuring a sample and outputting measurement result data, and a processing computer for processing the measurement result data output from the measurement unit; a setting information management device for storing setting information of a program introduced to the processing computer of the analyzer; and a computer readable portable storage medium storing a backup program; wherein the backup program is configured to cause the processing computer to function as, setting information acquiring means for acquiring setting information of the program introduced to the processing computer in which the backup program is executed from the processing computer when the backup program is executed by the processing computer of the analyzer, and storage means for storing the setting information acquired by the setting information acquiring means in the storage medium; and the backup program is configured to cause a computer to function as transmission means for transmitting the setting information stored in the storage medium to the setting information management device.

A third aspect of the present invention is a setting information management device for managing setting information of a program introduced to an analyzer for analyzing a sample, the setting information management device comprising: a database for storing specific information for specifying an analyzer and setting information of a program introduced to the analyzer specified by the specific information in correspondence to each other for every plurality of analyzers; reception means for receiving the specific information for specifying the analyzer and the setting information of a program introduced to the analyzer specified by the specific information from an external communication device; and registration means for registering the specific information and the setting information received by the reception means in the database.

A fourth aspect of the present invention is a setting information management method executed by a backup program stored in a portable storage medium by a processing computer of an analyzer; the method comprising the steps of: determining a type of the analyzer in which the backup program is executed from a plurality of types of analyzers; acquiring setting information of a program introduced to the processing computer based on the determination result; and storing the acquired setting information in the portable storage medium.

A fifth aspect of the present invention is a computer program product storing a backup program executable by a plurality of analyzers, the computer program product comprising: a portable storage medium; and instructions, on the portable storage medium, adapted to enable a general purpose computer to perform operations comprising: step of acquiring setting information of a program introduced to a processing computer in which the backup program is executed from the processing computer when the backup program is executed by the processing computer of the analyzer; step of storing the acquired setting information in the storage medium; and step of transmitting the setting information stored in the storage medium to the setting information management device when the backup program is executed by a computer communicably connected with the setting information management device storing the setting information.

BRIEF DESCRIPTION OF THE DRAWINGS

FIG. 14 is a list of setting value file acquired in the setting value acquiring process;

FIG. 15 is a list of setting value file (ipconfig.doc)

FIG. 17 is a flowchart showing a processing procedure of transmitting the setting value registered in the database of the management device to the transmission/reception computer.

DETAILED DESCRIPTION OF THE PREFERRED EMBODIMENTS

The preferred embodiments of the present invention will be described hereinafter with reference to the drawings.

Figure 1:
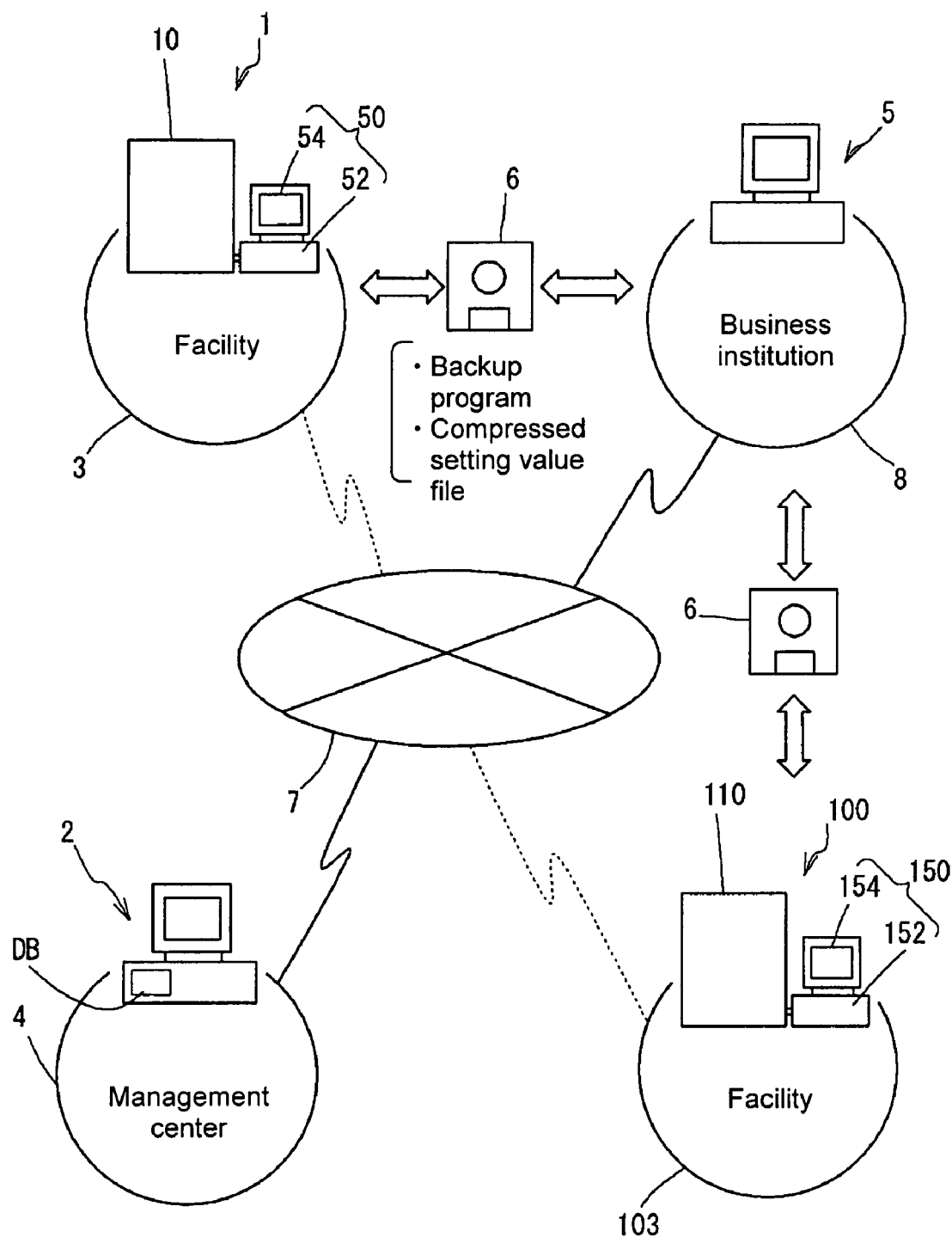
FIG. 1 is a view showing a configuration of a setting information management system according to an embodiment of the present invention.

FIG. 1 is a view showing a configuration of a setting information management system according to an embodiment of the present invention. The outline of the setting information management system of the present embodiment will be described with reference to the drawing. The setting information management system includes an analyzer 1, 100 for measuring or analyzing the sample, and a management device 2 for uniform managing various setting values (setting information) of the analyzers 1, 100 and other analyzers (not shown). The analyzers 1 and 100 are installed at a location (building) physically distant from the management device 2. For instance, the analyzer 1 is installed in a facility 3 such as hospitals and universities, the analyzer 100 is installed in a facility 103 different from the facility 3, and the management device 2 is installed in a management center 4 for maintenance service by the manufacturing company etc. of the analyzer 1. Various setting values of the analyzer 1 are exchanged between the analyzer 1 and the management device 2, where a transmission/reception computer 5, a removable (detachable, portable) storage medium 6 for storing a program (backup program), a network 7, and the like are interposed in such exchange.

The transmission/reception computer 5 is installed in a business institution 8 or a selling office arranged in the district for maintenance service or the facility 3, and is connected to the management device 2 of the management center 4 with a secure network 7 such as in-company LAN, dedicated line and VPN. The program of the storage medium 6 is used to perform a task of acquiring various setting values from the analyzer 1 of the facility 3 or restoring the setting values to the analyzer 1, and a task of transmitting/receiving the setting values through the network 7 between the transmission/reception computer 5 and the management device 2 or a computer (not shown) of a DB (database) administrator in the business institution 8. The detailed contents of the analyzers 1 and 100, the management device 2, and the storage medium 6 (dedicated program) will be described below.

[Configuration of the Analyzer 1, 100]

The setting information management system can use various types of analyzers such as blood cell analyzer, urine component analyzer, immune analyzer, biochemical immunoanalyzer, and the like. The system can also be used in different types of the same blood cell analyzer. The analyzers 1 and 100 according to the present embodiment are multi-item blood cell analyzer. The multi-item automatic blood cell analyzers 1 and 100 measure the blood or the specimen (sample), and analyze the measurement result. The analyzer 1 is configured by a measurement unit 10 for measuring the blood cell in the blood and a processing computer 50 for performing the process of the measurement result.

The measurement unit 10 measures a blood cell count item (CBC), a white blood cell classification item (DIFF), and a blood reticulocyte item (RET) of the blood sample through an electrical resistance method and a flow cytometer method using a semiconductor laser. The CBC item contains number of red blood cells (RBC), number of white blood cells (WBC), number of blood platelets (PLT), hemoglobin quantity (HGB), hematocrit value (HCT), and the like. The measurement unit 10 and the processing computer 50 are connected to enable data transmission with each other in a TCP/

IP method, which is one type of communication protocol, by way of a communication line 40.

[Configuration of Measurement Unit 10]

Figure 2:
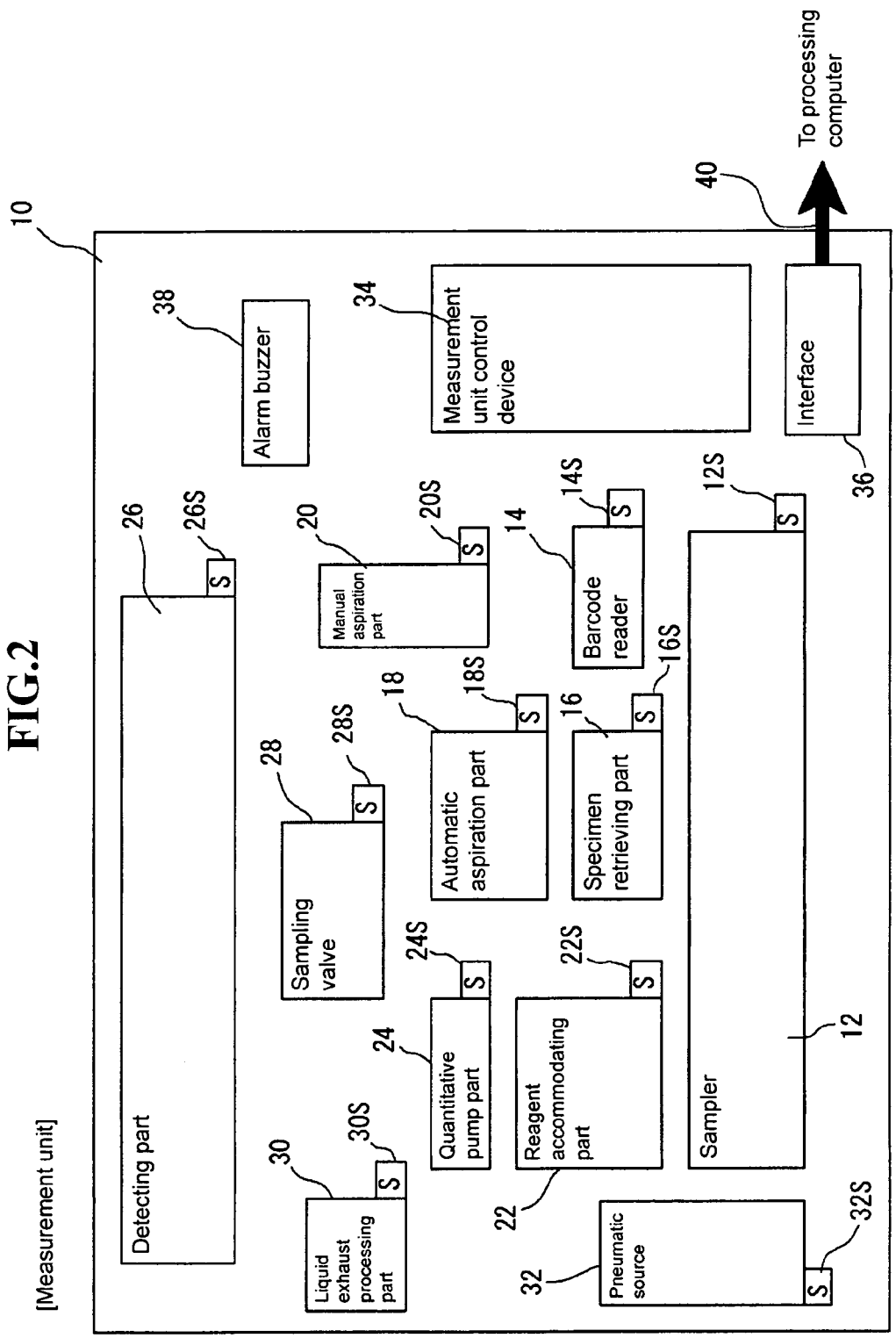
FIG. 2 is a view showing a configuration of a measurement unit of a multi-item automatic blood cell analyzer.

FIG. 2 is a view showing a configuration of the measurement unit 10 of the multi-item automatic blood cell analyzer 1. In such apparatus 1, the blood collected in a specimen container held in a specimen rack (not shown) can be analyzed. The measurement unit 10 is configured by a rack conveyance part 12 for conveying the specimen rack and automatically setting the same at a predetermined position; a barcode reader 14 for reading a barcode attached to the specimen rack; a specimen retrieving part 16 for retrieving the specimen container from the specimen rack; an automatic aspiration part 18 for automatically aspirating the specimen (blood) from the retrieved specimen container; a manual aspiration part 20 for aspirating the specimen from the set specimen container by hand; a reagent accommodating part 22 for accommodating a plurality of reagents; a quantitative pump part 24 for retrieving the reagent necessary for the test from the reagents accommodated in the reagent accommodating part 22; a detecting part 26 for measuring the blood cell count item, a white blood cell classification item (DIFF), and a blood reticulocyte item; a sampling valve 28 for quantifying and sending the reagent and the specimen of a necessary amount to the detecting part 26; a liquid exhaust processing part 30 for temporarily storing and exhausting the reagent and the specimen after measurement; a pneumatic source 32 for supplying pressure to each part that requires pressure gas such as valve, a sensor of each part (sensor 12S to sensor 32S), arranged in each part, for monitoring the operation state thereof; a measurement unit control device 34 for acquiring information from the sensor of each part and operation controlling each part in the measurement unit 10, analyzing data obtained through measurement, and acquiring measurement result data; and an interface 36 for TCP/IP connecting the measurement unit control device 34 to the processing computer 50 (FIG. 1). Furthermore, an alarm buzzer 38 for issuing an alarm sound in response to a signal via the measurement unit control device 34 when troubles occur in each part, and issuing an alarm sound (error sound) when determined that the input is not appropriate in the processing computer 50, as hereinafter described, is arranged.

Therefore, the measurement unit 10 is configured so that each part (component) described above cooperate with each other to execute the operation necessary for the measurement. The measurement unit 10 can transmit the measurement result and the other information to the processing computer 50, and receive operation command and the other information from the processing computer 50.

[Configuration of Processing Computer 50]

Figure 3:
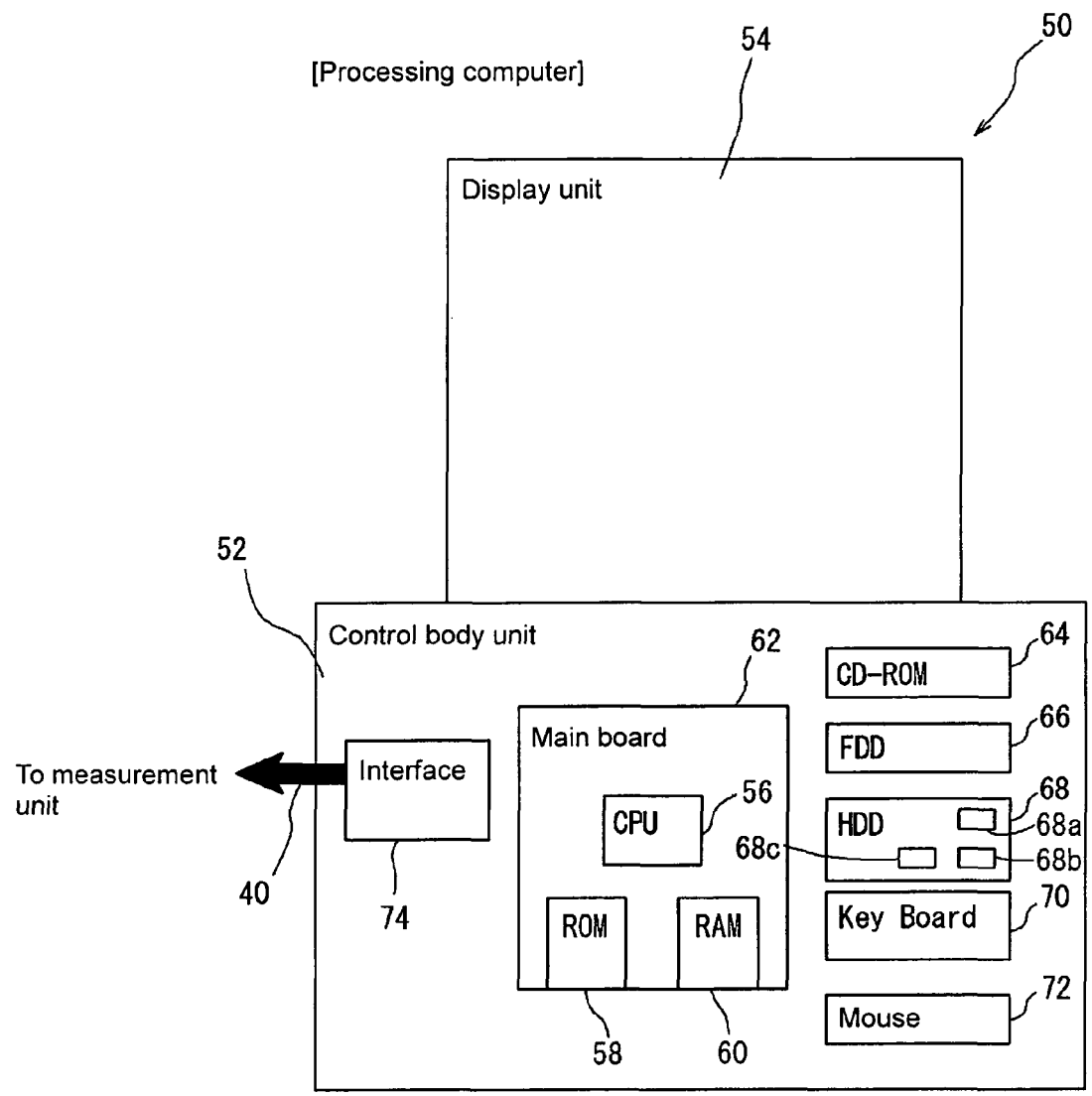
FIG. 3 is a view showing a configuration of a processing computer of the multi-item automatic blood cell analyzer.

FIG. 3 is a view showing a configuration of the processing computer 50 of the multi-item automatic blood cell analyzer 1. The processing computer 50 mainly includes a body unit 52 and a display unit (display device) 54, and performs a display process of the measurement result received from the measurement unit 10, a process of transmitting the operation command to the measurement unit 10, a process of displaying an operation screen of the analyzer 1 on the display unit 54, and other processes.

The body unit 52 includes a main board 62 for mounting a CPU 56, a ROM 58, and a RAM 60, a CD-ROM drive 64, a floppy (registered trademark) disc drive (hereinafter referred to as FD drive) 66, and a hard disc drive (hereinafter referred to as HDD) 68. The body unit 52 includes a keyboard 70 serving as an input part, and a mouser 72. The body unit 52 includes an interface 74 for TCP/IP connecting with the measurement unit 10.

The body unit 52 can use a commercially available personal computer in which an operating system (hereinafter referred to as OS) 68a such as Windows (registered trademark) is installed in the HDD 68. A display device such as TFT color liquid crystal display device and CRT is used in the display unit 54. A touch screen having an input function may be used for the display unit 54. The CPU 56 executes an analyzing program, to be hereinafter described, so that the operation screen including the display of various icons for inputting the command to cause the analyzer 1 to perform various operations is displayed on the display unit 54. From the operation screen, the user inputs the operation command to output the operation command to the measurement unit 10 via the interface 74. The body unit 52 receives the measurement result data and the operation state data etc. of the device transmitted from the measurement unit 10 via the interface 74, and displays the result of analysis of the specimen and the operation state of the device on the display unit 54.

A series of processes such as the operation control described above, that is, input of the operation command by the user, output of the operation command, reception of measurement result data sent from the measurement unit, operation state data of the device etc., the display of the result of analysis, and the like are realized by the processing computer 50 by executing the analyzing program 68b installed in the HDD 68. The analyzing program 68b is an application program operating on the OS.

The configuration of the multi-item automatic blood cell analyzer 100 will now be described. The analyzer 100 is configured by a measurement unit 110 for measuring the blood cell in the blood and a processing computer 150 for performing the process of the measurement result.

The measurement unit 110 measures the CBC item, the DIFF item, and the RET item, similar to the above described analyzer 1 of the blood sample through the electrical resistance method and the flow cytometry method using the semiconductor laser.

The measurement unit 110 and the processing computer 150 are connected to enable data transmission with each other in the TCP/IP method, which is one type of communication protocol, by way of the communication line 40.

[Configuration of Measurement Unit 110]

Figure 4:
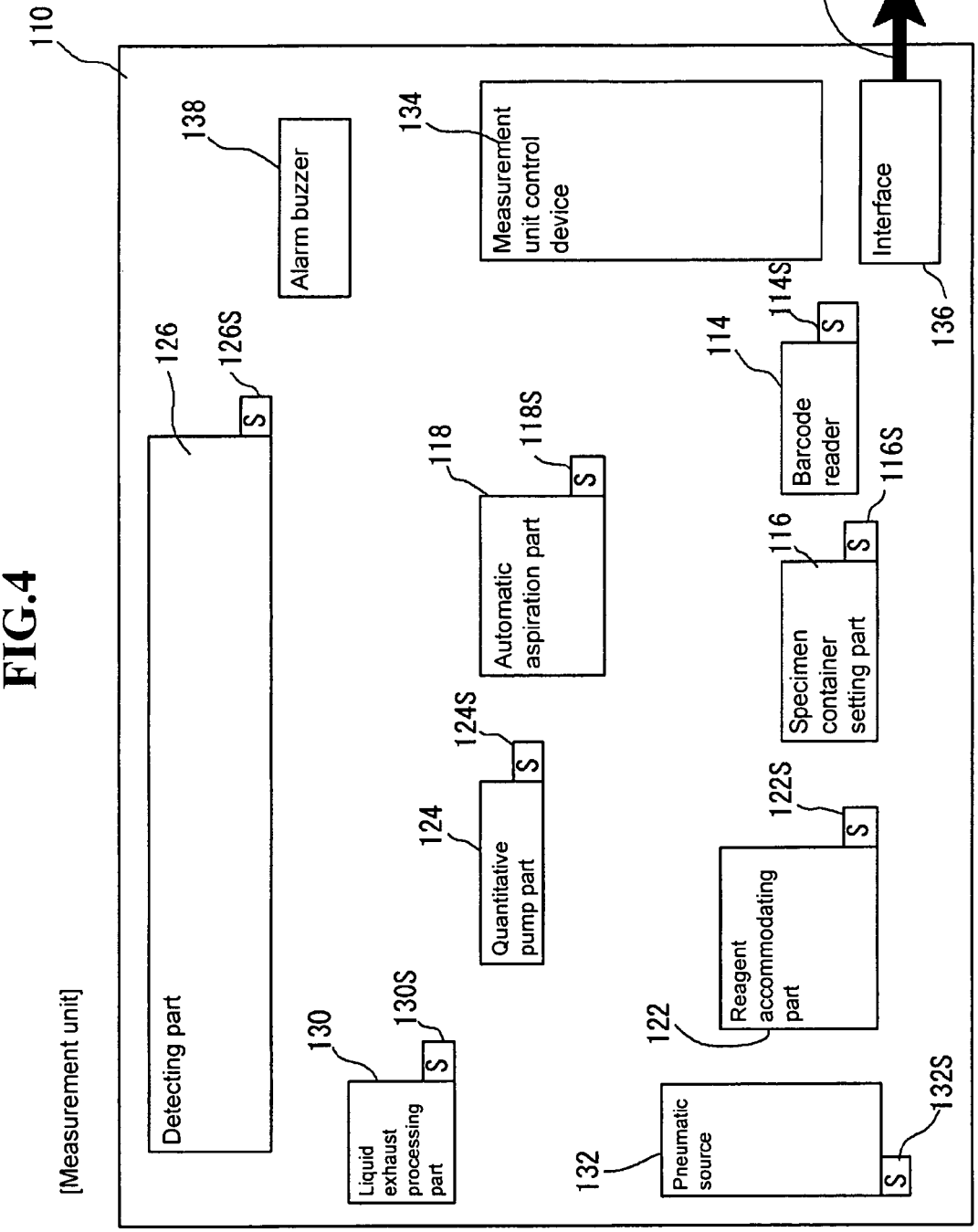
FIG. 4 is a view showing a configuration of the measurement unit of another multi-item automatic blood cell analyzer.

FIG. 4 is a view showing a configuration of the measurement unit 110 of the multi-item automatic blood cell analyzer 100. In the present apparatus, the analysis of the blood collected in a specimen container (blood collecting tube) can be performed. The measurement unit 110 is configured by a barcode reader 114 for reading a barcode attached to the specimen rack; a specimen container setting part 116 for retrieving the specimen container to the inside of the measurement unit 110 to aspirate the specimen and feed the specimen container completed with aspiration of the specimen to the outside of the measurement unit 110; an automatic aspiration part 118 for automatically aspirating the specimen (blood) from the specimen container retrieved by the specimen container setting part 116; a reagent accommodating part 122 for accommodating a plurality of reagents; a quantitative pump part 124 for retrieving the reagent necessary for the test from the reagents accommodated in the reagent accommodating part 122; a detecting part 126 for measuring the blood cell count item, a white blood cell classification item, and a blood reticulocyte item; a liquid exhaust processing part 130 for temporarily storing and exhausting the reagent and the specimen after measurement; a pneumatic source 132 for supplying pressure to each part that requires pressure gas such as valve, a sensor of each part (sensor 114S to sensor 132S), arranged in each part, for monitoring the operation state thereof; a measurement unit control device 134 for acquiring information from the sensor of each part and operation controlling each part in the measurement unit 110, processing the signal output from the detecting part 126, and acquiring measurement result data, and an interface 136 for TCP/IP connecting the measurement unit control device 134 to the processing computer 150 (FIG. 1). Furthermore, an alarm buzzer 138 for issuing an alarm sound in response to a signal via the measurement unit control device 134 when troubles occur in each part, and issuing an alarm sound (error sound) when determined that the input is not appropriate in the processing computer 150, as hereinafter described, is further arranged. In such analyzer 100, the necessary amount of specimen is quantified in the automatic aspiration part 118 and the necessary amount of reagent is quantified in the quantitative pump part 124, which specimen and reagent are mixed and sent to the detecting part 126.

Therefore, the measurement unit 110 1 is configured so that each part (component) described above cooperate with each other to execute the operation necessary for the measurement. The measurement unit 110 can transmit the measurement result and the other information to the processing computer 150, and receive operation command and the other information from the processing computer 150.

[Configuration of Processing Computer 150]

Figure 5:
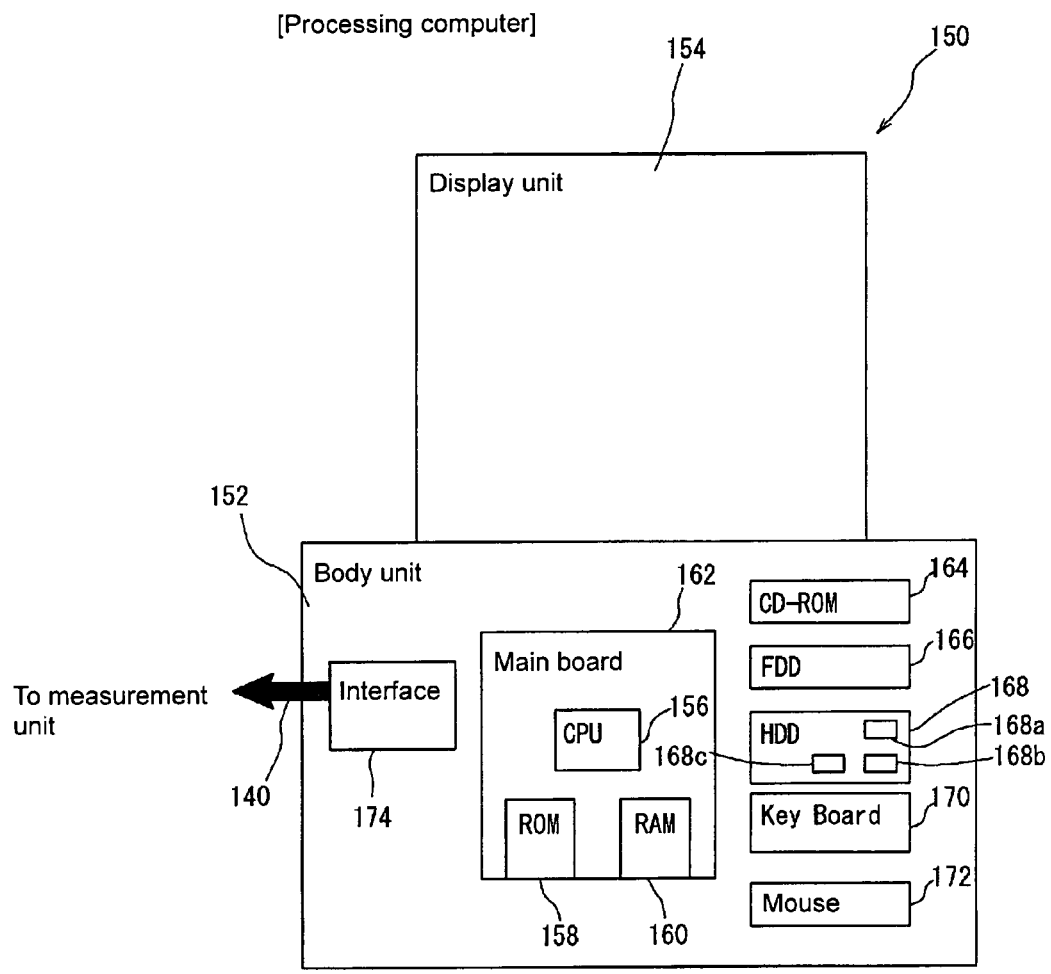
FIG. 5 is a view showing a configuration of a processing computer of another multi-item automatic blood cell analyzer.

FIG. 5 is a view showing a configuration of the processing computer 150 of the multi-item automatic blood cell analyzer 100. The processing computer 150 has an operating system 168*a* and an analyzing program 168*b* installed in the hard disc drive 168. When the CPU 156 executes the analyzing program 168*b*, processes such as input of operation command by the user, output (transmission) of the operation command, reception of measurement data sent from the measurement unit, operation state data etc. of the device, analysis of measurement data, display of result of analysis, and the like are performed. The analyzing program 168*b* is an application program operating on the OS. Other configurations of the processing computer 150 are the same as the configurations of the above described processing computer 50, and thus the description thereof will be omitted.

As described above, a general-purpose computer can be used for the hardware of a personal computer configuring the processing computer 50, 150 since the analyzing program is an application program operating on the OS in the analyzers 1 and 100. The revision task of the analyzing program can be easily performed by allowing the analyzing program to be installed to the computer on the user side.

The OS and the analyzing program installed in the HDD 68, 168 of the body unit 52, 152 contains various setting values (setting information). For example, the analyzing program contains various setting values such as measurement setting value unique to the analyzer 1, an analysis setting value, and an output setting value such as measurement data and result of analysis. The OS contains setting values related to the communication protocol such as TCP/IP, setting values related to the driver controlling peripheral equipments, and the like. An auxiliary program 68*c*, 168*c* such as a remote operation program for remote operating the analyzer 1 other than the OS 68*a*, 168*a* and the analyzing program 68*b*, 168*b* is installed in the HDD 68, 168 of the body unit 52, 152, and various setting values are contained in such auxiliary program.

In introducing the analyzers 1, 100 to the facilities 3, 103, the analyzers 1, 100 are delivered to the facilities 3, 103 with the analyzing program 68*b*, 168*b*, the auxiliary program 68*c*, 168*c*, and the OS 68*a*, 168*a* installed in the HDD 68, 168 of the body unit 52, 152 in advance. The analyzers 1, 100 become operable when the technician inputs the necessary setting values for the program.

In the setting information management system of the present embodiment, when the analyzers 1, 100 become operable as described above, the setting values for the various programs are acquired (backed up) from the analyzers 1, 100, and transmitted to the management device 2 (FIG. 1) to perform remote management. The setting values are received from the management device 2, as necessary, and restored in the control units of the analyzers 1, 100. The function of acquisition of the setting values, transmission/reception, and restoration are realized by using a backup program to be described in detail below. In the following description, only a case of backing up the setting values of the analyzer 1 by the backup program will be described for the sake of simplifying the description, but the case of backing up the setting values of the other analyzer 100 takes similar procedures.

As shown in FIG. 1, the backup program is stored in a removable storage medium 6 exemplified with the floppy (registered trademark) disc (hereinafter referred to as FD). The FD 6 is inserted into the FD drive 66 (FIG. 3) of the processing computer 50 of the analyzer 1 to execute the backup program in the processing computer 50.

The backup program is configured to realize, by means of the processing computer 50, the function serving as a determining means for determining the type of the analyzer 1 where the backup program is executed, the function serving as an acquiring means (setting information acquiring means) for acquiring the setting value (setting information) of the program introduced into the processing computer 50 of the analyzer 1 from the processing computer 50 based on the determination result, and the function serving as a storage means for storing the acquired setting value to the storage medium 6. The backup program is configured to realize, by means of the transmission/reception computer 5 installed in the business institution 8 (FIG. 1), the function serving as a transmission means for transmitting the setting value stored in the storage medium 6 and a reception means for receiving the setting value from the management device 2, and the like. The transmission means and the reception means can be realized with the processing computer 50 installed in the facility 3 and other computers if the management center 4 and the facility 3 are connected through the network 7.

[Details of Backup Program]

Figure 6:
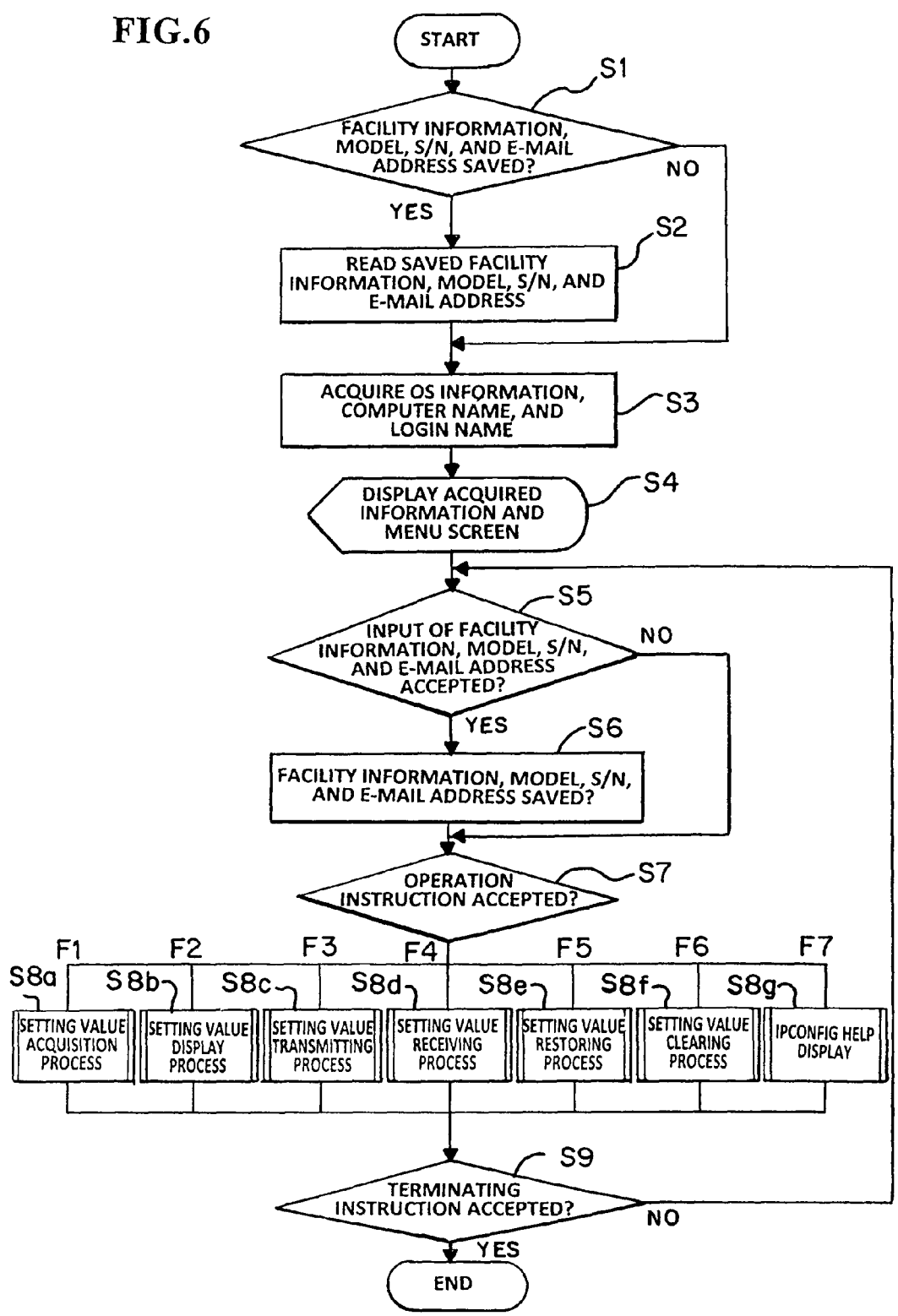
FIG. 6 is a flowchart showing a processing procedure of the CPU when a backup program is executed.

FIG. 6 is a flowchart showing a processing procedure of the CPU when executing the backup program. The technician inserts the FD 6 recorded with the backup program to the FD drive 66 of the processing computer 50, and displays the file saved in the FD 6 on the display unit 54 using the disc display program (My Computer etc.) equipped in the OS. A file "MENU shortcut" existing in the displayed files is double clicked to be executed (activated), and the backup program is executed. When the backup program is executed, the CPU 56 determines whether or not facility information, model, S/N (serial number), address of the transmitter are already saved in the FD 6 in step S1. If such information are saved, the CPU 56 reads such information to the storage unit such as RAM 60 of the processing computer 50 (step S2). When installing the analyzer 1 in the facility 3, and performing the operation of acquiring the setting value for the first time, the facility information, model, S/N (serial number), and address of the transmitter are not saved in the FD 6, and thus are not read, and the process proceeds to step S3. In step S3, the CPU 56 acquires the type of OS, OS information such as version, computer name (terminal name), and login name when logged into the processing computer 50 from the storage unit of the processing computer 50. In step S4, the CPU 56 displays a menu screen W, to be hereinafter described, on the display unit 54 of the processing computer 50. Information (terminal name and login name) acquired in step S3 is displayed at the lowermost part of the menu screen W. The acquired OS information is used in the setting value acquiring process to be hereinafter described.

Figure 7:
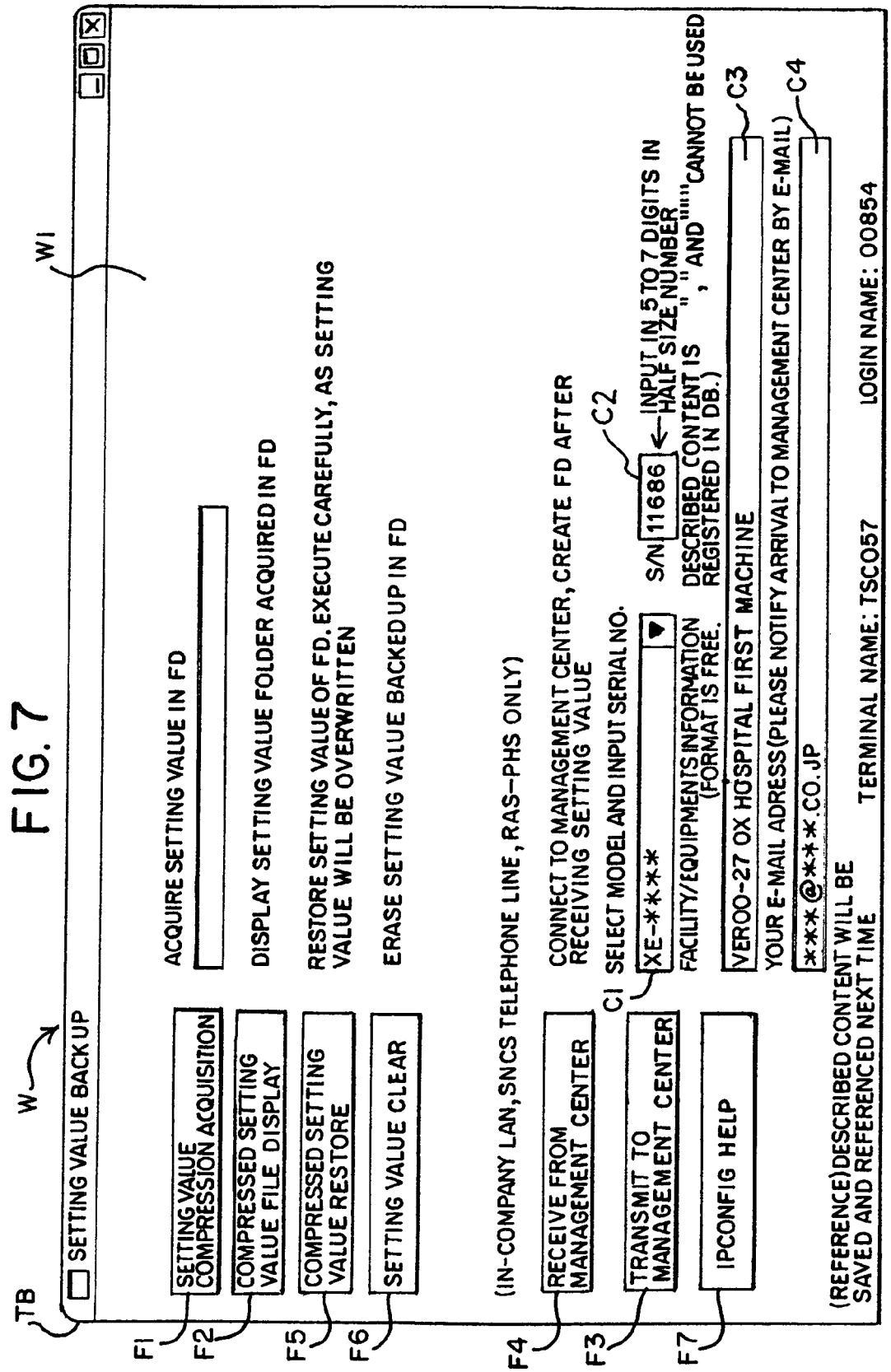
FIG. 7 is a frame format view showing a menu screen W (operation screen) displayed on a display unit when the backup program is executed.

FIG. 7 is a frame format view showing the menu screen W (operation screen) displayed on the display unit 54 of FIG. 3 when the backup program is executed. A title bar TB displaying the program name ("set vale BACKUP") is arranged at the upper end of the menu screen W, and a plurality of function buttons (icons) F1 to F7 are arrayed in the up and down direction on the left side of the function display unit W1 of the lower side. Each function of the backup program is executed when the technician select (click) the function buttons F1 to F7. The function button includes, in the order from the top, "setting value compression acquisition" button F1, "compressed setting value file display" button F2, "compressed setting value restore" button F5, "setting value clear" button F6, "receive from management center" button F4, "transmit to management center" F3, and "ipconfig help" button F7. The function buttons of F1, F2, and F5 to F7 are executed by the processing computer 50 of the analyzer 1, and the function buttons of F3, F4 are executed by the transmission/reception computer 5 of the business institution 8 (transmission/reception computer in the facility 3 in some cases). The description of each function is character displayed on the right side of the function buttons F1, F2 and F4 to F6, and input fields C1 to C4 for manually inputting information are arranged on the right side of the function button of F3.

The technician can newly input the facility information, model, S/N (serial number), and the address of the transmitter to the input fields C1 to C4. In step S5 of FIG. 6, the CPU 56 determines whether or not the facility information, model, S/N (serial number), and the address of the transmitter are accepted. The model name (C1) has the model names of the analyzer 1, to which the backup program corresponds, listed in a pull down menu to be selected therefrom. The facility/equipment information (C3) is written by the technician so as to be distinguishable from the other facility by a third person. The model name (C1) and the serial number (C2) are specific information for specifying the analyzer 1. In the present embodiment, a configuration in which the technician manually inputs the model name and the serial number is described, but is not limited thereto, and the model name and the serial number can be automatically acquired from the processing computer 50 and automatically input. The input of information to the input fields C1 to C4 can be carried out in the transmission/reception computer 5 during the transmitting process of the setting value to be hereinafter described. Thus, when accepting input of facility information, model, S/N, and the address of the transmitter by the technician, the CPU 56 saves the input information in the FD 6 in step S6, and proceeds the process to step S7.

In FIG. 6, the CPU 56 determines whether or not the operation instruction is accepted, that is, whether or not selection of one of the function buttons F1 to F7 is accepted (step S7). When accepting the selection of the function button F1, that is, when the technician selects (clicks) the "setting value compression acquisition" button F1 arranged on the uppermost position in the menu screen W of FIG. 7, the CPU 56 executes the setting value acquisition process described in detail below (step S8a).

[Setting Value Acquisition Process]

Figure 8:
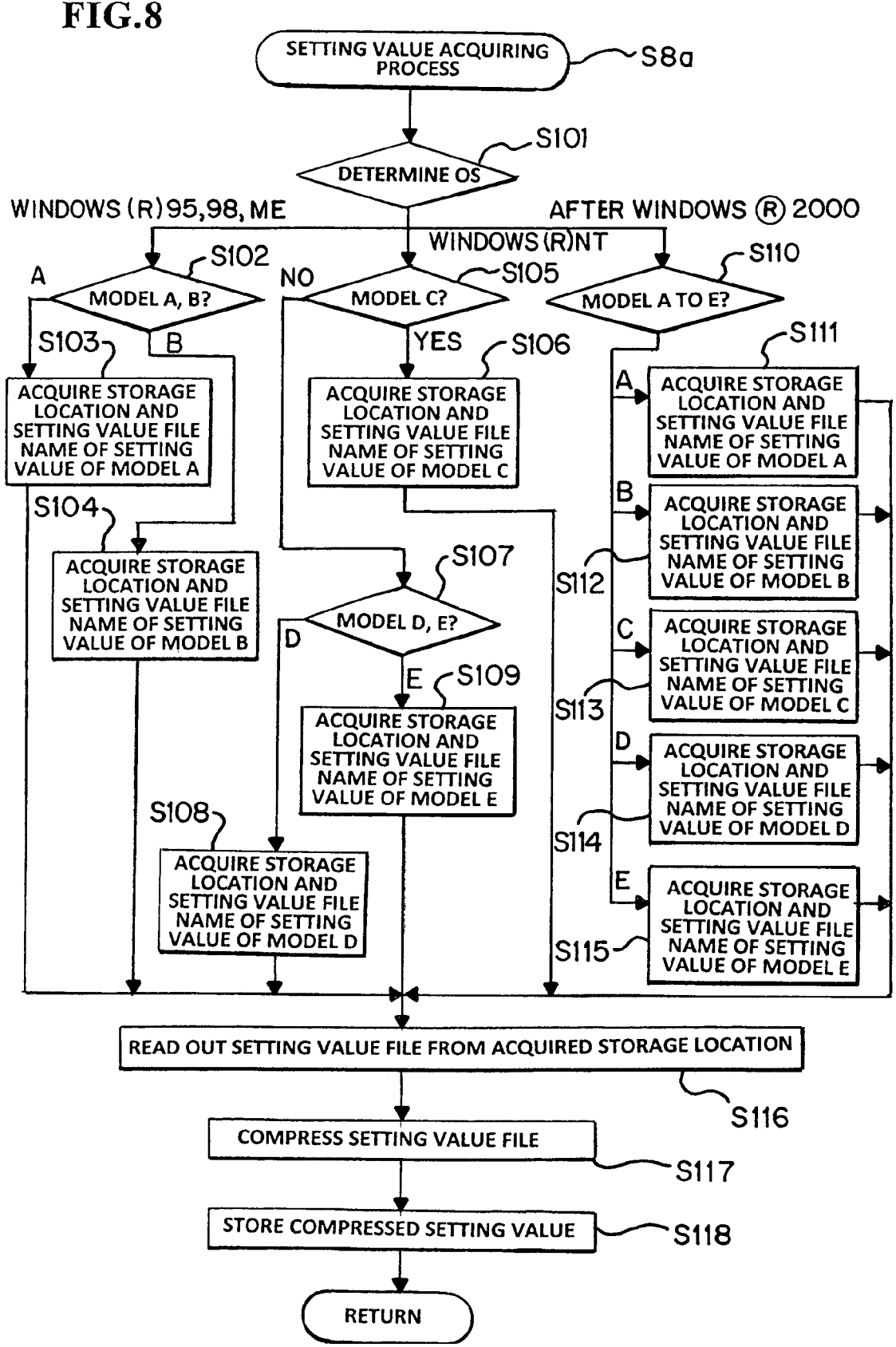
FIG. 8 is a flowchart showing a processing procedure of a setting value acquisition process.

FIG. 8 is a flowchart showing a processing procedure of the setting value acquisition process. The setting value acquisition process causes the computer 50 to execute the function serving as the determining means and the setting information acquiring means, and the function serving as the storage means. In step S101, the CPU 56 of the processing computer 50 determines the type of OS introduced to the processing computer 50. The CPU 56 then determines the model of the analyzer 1 for every type of OS in steps S102, S105, and S110. In other words, the CPU 56 acquires specific information specifying the type of analyzer. This is based on the following reasons.

The setting value of each program introduced to the processing computer 50 has different storage location (directory) of the processing computer 50 according to the model of analyzer. The name of the file where the setting value is stored also differs according to the model of the analyzer. Therefore, the setting value acquisition process corresponding to the model needs to be performed, and to this end, the model must be determined. However, since the processing speed of the model using an old processing computer 50 is slow, it takes a very long time if the determination process is performed for all the models the analyzer 1. The type (version) of the OS introduced to the processing computer 50 differs depending on the model and the release period of the analyzer 1, but which OS is introduced in which model is defined. Thus, in the present embodiment, determination of the OS is first performed, and determination is carried out narrowing to the model introduced with the relevant OS, so that high speed process can be realized even in the old processing computer.

In the present embodiment, the type of OS to be determined that is assumed by the backup program is (α) Windows95, 98, Me, (β) Windows NT, (γ) Windows2000 or later (all of "Windows" are registered trademark). In the figure, there are five types A to E of models of the analyzer 1 to be determined. When the OS belongs to (α), the process proceeds to step S102, and determination is performed from the models corresponding to such OS. The model corresponding to the OS of group (α) is two models "A" and "B", where the CPU 56 determines one of the two models in step S102. If determined as model A in step S102, the CPU 56 acquires the storage location of the setting value file and the setting value file name of the model A in step S103. If determined as model B in step S102, the CPU 56 acquires the storage location of the setting value file and the setting value file name of the model B in step S104. The backup program contains information related to the storage location and setting value file name of the setting value of each program introduced to the processing computer in advance for every model and operating system of the analyzer, so that the processes of steps S103 and S104 are performed by acquiring such information.

When OS belongs to (β), the CPU 56 determines whether or not the model is a specific model "C" in which the introducing result of the OS is the greatest in step S105. If the model is "C", the CPU 56 acquires the storage location and setting value file name of the setting value file corresponding to the relevant model in step S106. If the model is not "C", the CPU 56 makes the determination from other models "D" and "E" corresponding to the OS in step S107. When determined as the model D, the CPU 56 acquires the storage location and the setting value file name of the setting value file of the model D in step S108. When determined as the model E, the CPU 56 acquires the storage location and the setting value file name of the setting value file of the model E in step S109. The specific OS corresponds to the plurality of models, but if the number of specific models is very large, high processing efficiency can be ensured by distinguishing between the model in which the introducing result is large and the model in which the introducing model is small, as shown in steps S105, S107.

When the OS belongs to (γ), the CPU 56 determines the model from all the models ("A" to "E") introduced with the OS in step S110. This is because the OS belonging to (γ) is relatively new, and the processing computer 50 introduced with the OS is assumed to have high processing speed, and thus high processing becomes possible without distinguishing by models. After determining the model in step S110, the CPU 56 acquires the storage location and the setting value file name of the setting value file corresponding to the distinguished model in step S111 to S115. Both step S103 and step S111 acquire the storage location and the setting value file name of the setting value file of the model A, but are not the same processes. In step S103, the analyzing program operating on the Windows 95, 98, ME or the storage location and the setting value file name of the setting value file used in the Windows 95, 98, ME are acquired, whereas in step S111, the analyzing program operating on the Windows 2000, XP or the storage location and the setting value file name of the setting value file used in the Windows 2000, XP are acquired, where the storage location and the setting value file name acquired in the respective process differs.

As described above, after acquiring the storage location and the setting value file name of the setting value file that matches the model of the analyzer, the CPU 56 reads out the setting value file of the acquired file name from the acquired storage location in step S116. The CPU 56 then creates a compressed setting value file by compressing the read out setting value file (step S117), stores the compressed setting value file in the FD 6 (step S118), and returns the process.

The determining process of the model in the steps S102, S105, S107, and S110 is performed by determining whether or not a predetermined file for analyzing program exists in a predetermined directory, whether or not predetermined information (e.g., model name) exists in the predetermined database, or the like. When the setting value file is compressed as described above, the setting information can be efficiently saved in the FD 6 of small capacity, and the process of transmission/reception of the compressed setting value file, to be hereinafter described, can be performed in a short period of time.

The setting value file acquired in the setting value acquiring process is as shown in FIG. 14. In this figure, the file name of the setting value file recorded with the setting value, the program name using the setting value, the directory storing the setting value, the outline of the file, and the details of the file are shown.

Here, the setting value file (ipconfig.doc) of (a) is recorded with the setting value used in the OS, and is mainly recorded with the setting value for communication. Specifically, as shown in FIG. 15, information such as host name (computer name) or the communication information (Windows (registered trademark) NT IP Configuration) of the OS itself, the DNS server address, the node type, the NetBios scope ID, the valid/invalid of the IP routing, valid/invalid of WINS proxy, valid/invalid of the NetBIOS DNS, and the like are recorded. Furthermore, information such as name, physical address (MAC address), valid/invalid of DHCP, IP address, subnet mask, default gateway, and the like are recorded as information regarding the network equipment (Ethernet adapter) used in the processing computer 50.

The setting value file (remote.+++) of (b) in FIG. 14 is the setting value of the remote operation software (illustrated as "remote_program" as program name) or the auxiliary program, and the nickname of the facility 3 and the setting value unique to the facility regarding various connection settings are recorded. The setting value file of (c) is the setting value for transmission program for performing precision management and automatic monitoring of the analyzer 1 by the management center 4 using the network in the analyzing program (illustrated as "XE_program" as program name) used in the analyzer 1 of the model name "XE-****". The setting value file of (d) is the setting value related to the substantial analysis operation control such as measurement and analysis in the analyzing program of the analyzer 1, where the setting value for the printer, the host computer data output format, and the like are contained therein.

In FIG. 6, after the process of step S8a is terminated, the CPU 56 determines whether or not terminating instruction of the backup program is accepted in step S9, and the CPU 56 performs the process of closing the menu screen W and terminating the backup program when the terminating instruction is accepted. The CPU 56 returns the process to step S4 if the terminating instruction is not accepted.

[Setting Value Display Process]

Figure 9:
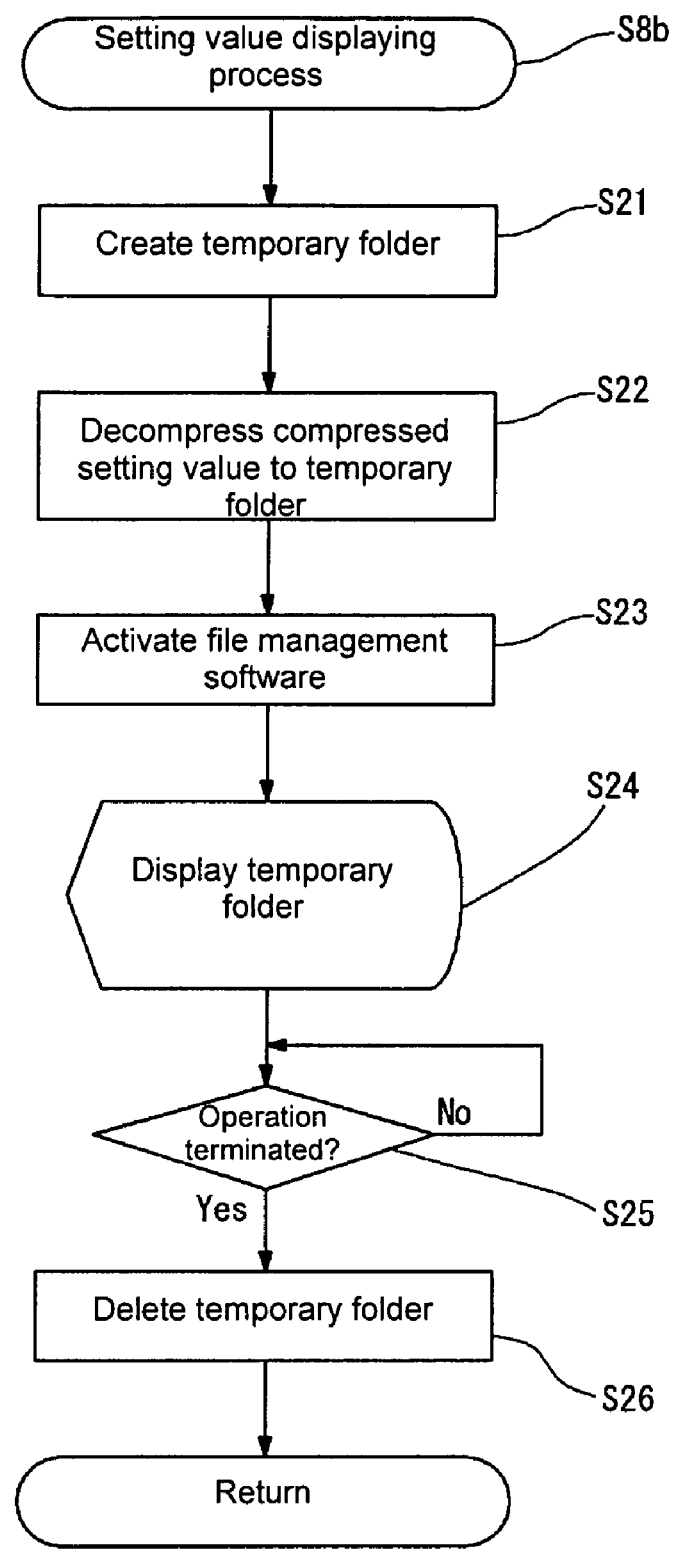
FIG. 9 is a flowchart showing a processing procedure of a displaying process of a compressed setting value file.

In FIG. 7, when the technician selects the "compressed setting value file display" button F2, the CPU 56 of the processing computer 50 accepts the selection of the relevant function button F2 in step S7 of FIG. 6, and performs the process of setting value display (step S8b). FIG. 9 is a flowchart showing the processing procedure of the setting value display process. In step S21, the CPU 56 creates a temporary folder that is temporarily used in the HDD 68. In step S22, the CPU 56 decompresses the compressed setting value file in the created temporary folder to obtain a state the setting value file can be displayed. In step S23, the CPU 56 activates the file management software such as Explorer, and in step S24, displays the setting value file name (file name listed in FIG. 14) in the temporary folder on the file management software. The user can easily check that the setting values are appropriately acquired by displaying the relevant screen. Thereafter, the CPU 56 accepts the termination of the file management software (step S25), automatically deletes the temporary folder (step S26), and returns the process to return the display to the menu screen W.

The backup task in the facility 3 is thereby terminated by acquiring the setting value file from the processing computer 50 of the analyzer 1 and storing the same in the FD 6.

[Transmitting Process of Setting Value]

As shown in FIG. 1, the FD 6 stored with the compressed setting value file in the facility 3 is brought back to the business institution 8 by the technician. The technician performs the task of transmitting the compressed setting value file stored in the FD 6 from the transmission/reception computer 5 of the business institution 8 to the management center 4. The transmission/reception computer 5 is a commercially available general-purpose computer, and has substantially the same configuration as the processing computer 50 shown in FIG. 3. However, a communication cable for connecting to the network 7 is connected to the interface 74.

The transmitting process of the setting value is carried out by executing the backup program stored in the FD 6 on the transmission/reception computer 5, and causing the transmission/reception computer 5 to function as a transmission means for transmitting the setting information. In the menu screen W (FIG. 7) of the backup program, the technician inputs the necessary information to the input fields C1 to C4 as described in step S5 (FIG. 6) above prior to the transmission of the compressed setting value file of the analyzer 1.

Figure 10:
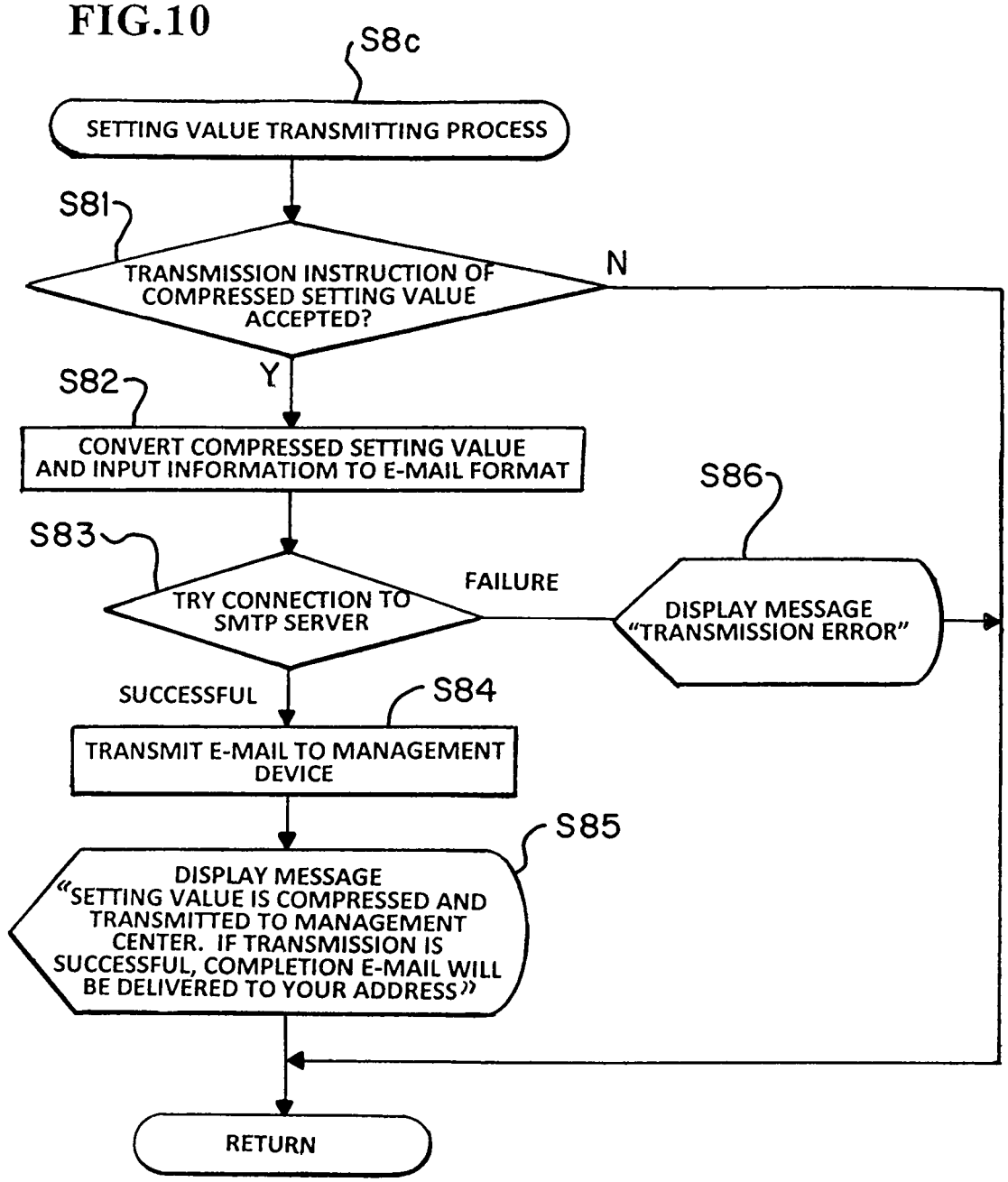
FIG. 10 is a flowchart showing a processing procedure of a transmitting process of the compressed setting value file.

When the technician selects the "transmit to management center" button F3 in the menu screen W, the CPU of the transmission/reception computer 5 accepts the selection of the relevant button F3 and thereafter performs the process of step S8c in step S7 of FIG. 6. FIG. 10 is a flowchart showing a processing procedure of the process of step S8c, that is, the setting value transmitting process. The CPU of the transmission/reception computer 5 determines whether or not the instruction to transmit the compressed setting value file to the management center 4 is accepted in step S81. In the process of step S81, specifically, a screen (not shown) for checking whether the compressed setting value file can be transmitted is displayed, and the transmission instruction of the compressed setting value file is accepted in the relevant screen. The "Y (Yes)" button and the "N (No)" button are arranged on the screen, where when the technician selects the "Y (Yes)" button, the CPU proceeds the process to step S82, and when the technician selects the "N (No)" button, the CPU returns the process and returns the display to the menu screen W.

In step S82, the CPU of the transmission/reception computer 5 converts the compressed setting value file saved in the FD 6 and the information input to the input fields C1 to C4 of FIG. 7 to a format of e-mail. In step S83, the CPU of the transmission/reception computer 5 attempts the connection to the SMTP server operating in the network 7, and transmits the e-mail to the management device 2 of the management center 4 when connection is successful (step S84).

Thereafter, in step S85, the CPU of the transmission/reception computer 5 displays a message on the display unit "setting value is compressed and transmitted to the management center. If the transmission is successful, a completion e-mail will be delivered to your address", returns the process, and returns the display to the menu screen W (FIG. 7).

If the connection to the SMTP server fails in step S83, the CPU of the transmission/reception computer 5 displays the message on the display unit 54 "transmission error" in step S86, returns the process, and returns the display to the menu screen W. The compressed setting value file transmitted to the management center 4 is stored and managed in the management device 2 (FIG. 1) with specific information such as model name and serial number of the analyzer. The details thereof will be described later.

When performing replacement, initialization, and system update involved in failure etc. of the processing computer 50, the setting value of each program needs to be restored to the processing computer 50 of the analyzer 1. In this case, the technician first performs the task of receiving the compressed setting value file managed by the management device 2 by means of the transmission/reception computer 5. The receiving process of the compressed setting value file can be carried out by executing the backup program stored in the FD 6 on the transmission/reception computer 5. The backup program is configured to cause the transmission/reception computer 5 to function as a specific information transmission means for transmitting specific information of the analyzer 1 to the management device 2, a reception means for receiving the compressed setting value file corresponding to the transmitted specific information from the management device 2, and a storage means (second storage means) for storing the received setting information in the FD 6.

After receiving the compressed setting value file, the backup program is executed on the processing computer 50 in order to restore the file to the processing computer 50 of the analyzer 1. The backup program is configured to cause the processing computer 50 to function as a restoration means for restoring the setting value recorded in the compressed setting value file to the processing computer 50. The details of the receiving process and the restoring process of the setting value will be described below.

[Receiving Process of Setting Value]

In order to perform the receiving process of the compressed setting value file, first the backup program is executed on the transmission/reception computer 5, and the menu screen W of FIG. 7 is displayed on the display unit of the transmission/reception computer 5. The technician then inputs the model name and the serial number, which are specific information of the analyzer 1, to the input fields C1, C2 of the menu screen W (FIG. 7). When the technician selects the "receive from management center" button F4, the CPU of the transmission/reception computer 5 accepts the selection of the button F4 in step S7 of FIG. 6, and performs the process of step S8d.

Figure 11:
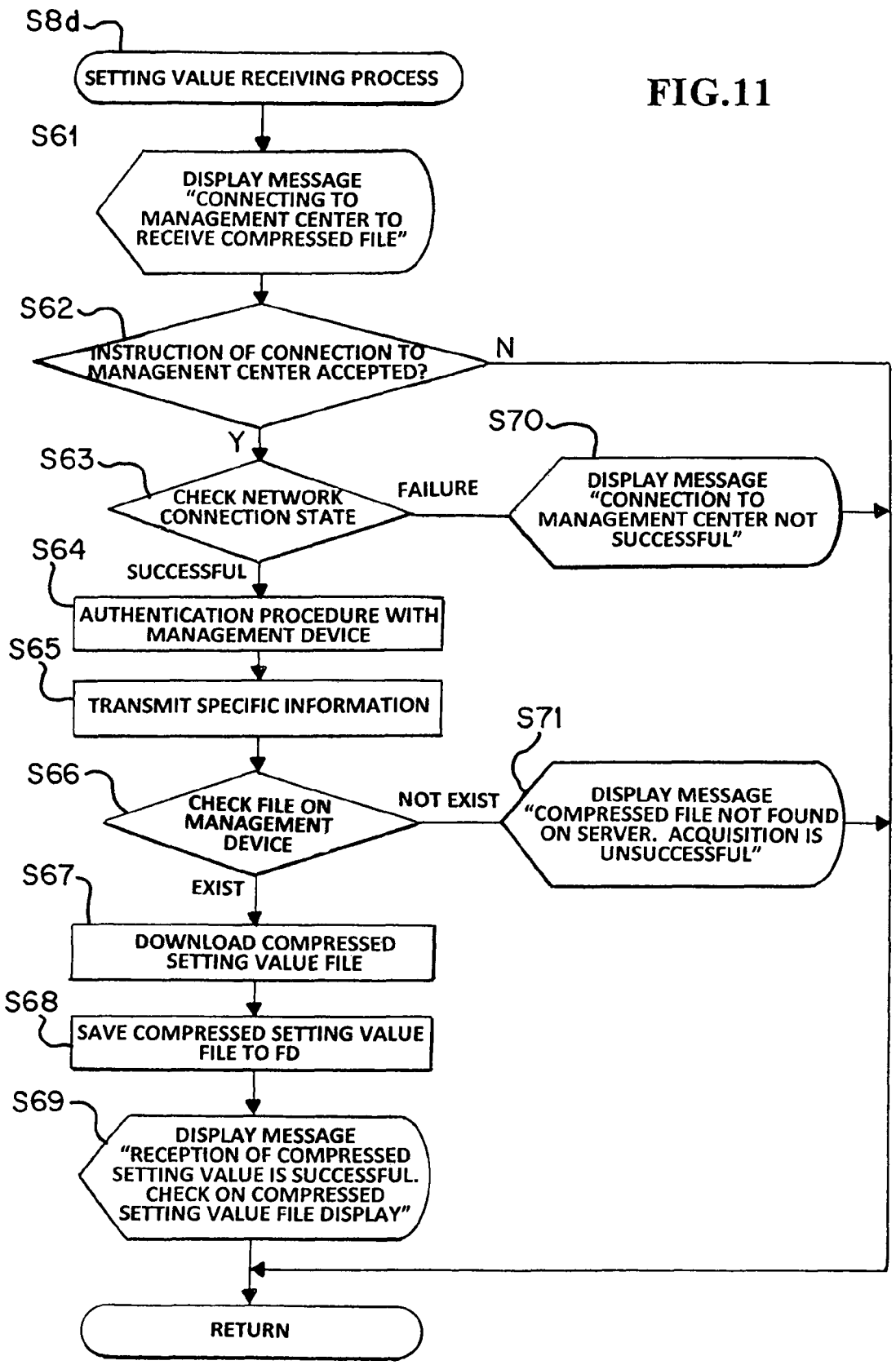
FIG. 11 is a flowchart showing a processing procedure of a receiving process of the compressed setting value file.

FIG. 11 is a flowchart showing a processing procedure of the process of step S8d, that is, the receiving process of the compressed setting value file. In step S61, the CPU of the transmission/reception computer 5 displays a message on the display unit "connecting to management center to receive compressed file", and determines whether or not connection instruction to the management center 4 is accepted (step S62). In step S62, a screen (not shown) for accepting the connection instruction to the management center 4 is displayed, and when the technician selects the "Y (Yes)" button on the screen, the CPU proceeds the process to step S64, and when the technician selects the "N (No)" button, the CPU returns the process and returns the display to the menu screen W.

In step S63, the CPU of the transmission/reception computer 5 performs a connection check to the network 7, and performs an authentication procedure with the management device 2 of the management center 4 when the connection is successful (step S64). In step S65, the CPU of the transmission/reception computer 5 transmits the specific information of the analyzer 1 to the management device 2, and determines whether or not the compressed setting value file of the analyzer corresponding to the specific information exists (step S66). If the compressed setting value file exists, the CPU of the transmission/reception computer 5 downloads the compressed setting value file in step S67. Thereafter, the CPU of the transmission/reception computer 5 performs the process of storing the compressed setting value file downloaded to the FD 6 in step S68, and displays a message "reception of compressed setting value is successful. Check on the compressed setting value file display" in step S69, returns the process, returns the display to the menu screen W (FIG. 7).

After receiving the compressed setting value file, in order to check the content thereof, the "compressed setting value file display" button F2 of the menu screen W is selected, and the process is performed with the procedures shown in FIG. 9. If the connection to the network 7 fails in step S63 of FIG. 11, the CPU displays a message on the display unit "connection to management center not successful" in step S70, returns the process, and returns the display to the menu screen W. Furthermore, if determined that the compressed setting value file does not exist on the management device 2 in step S66, the CPU displays a massage on the display unit "compressed file not found on the server. Acquisition is unsuccessful" in step S71, returns the process, and returns the display on the menu screen W.

[Restoring Process of Setting Value]

Figure 12:
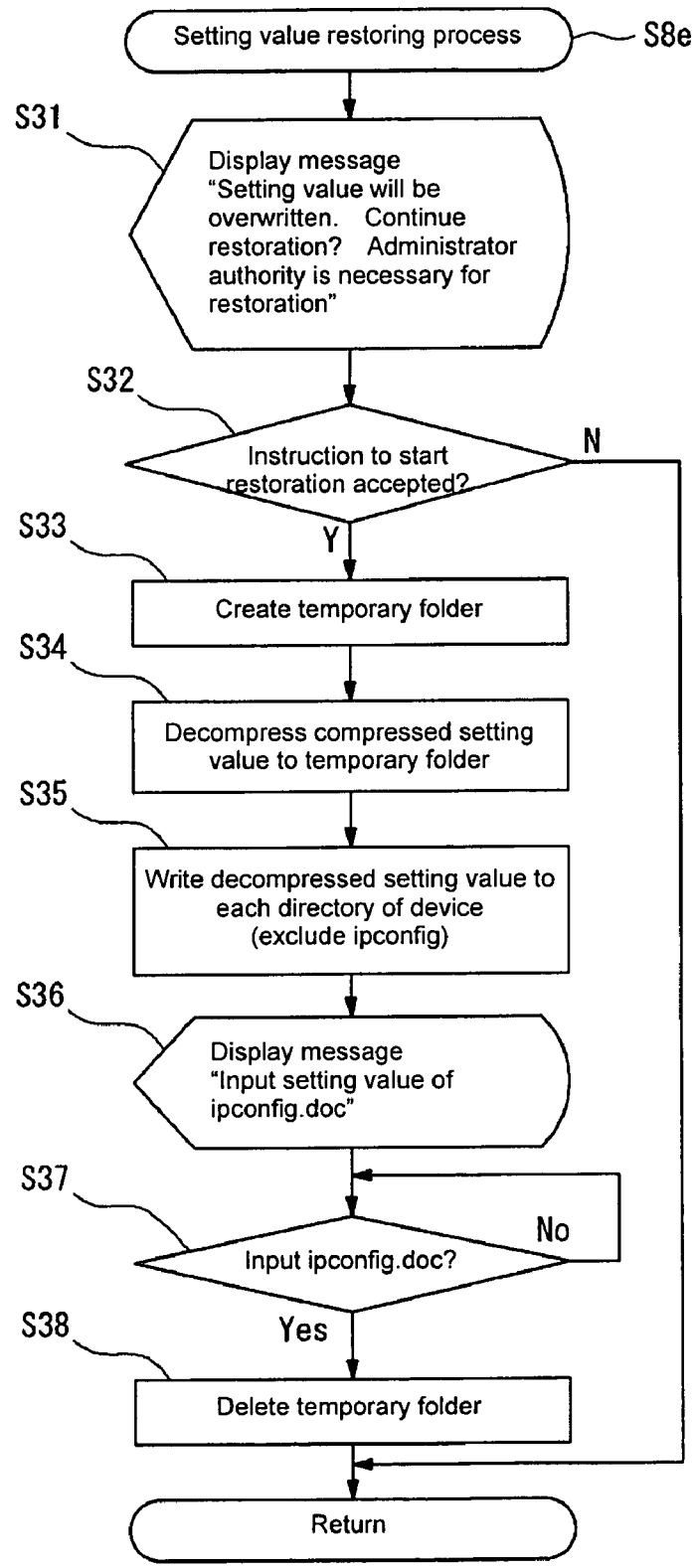
FIG. 12 is a flowchart showing a processing procedure of a restoring process of the compressed setting value file.

After receiving the compressed setting value file from the management device 2, the technician brings the FD 6 back to the facility 3 (FIG. 1), executes the backup program in the FD 6 on the processing computer 50 of the analyzer 1 attempting to perform restoration, and displays the menu screen W of the FIG. 7. When the technician selects the "compressed setting value restore" button F5 in the menu screen W, the CPU 56 of the processing computer 50 accepts the selection of the button F5 in step S7 of FIG. 6, and performs the process of step S8e. FIG. 12 is a flowchart showing a processing procedure of the process of step S8e, that is, the restoring process of the compressed set file. First, in step S31, the CPU 56 displays a screen for accepting the instruction to start restoration on the display unit 54, and accepts the instruction to start restoration on the screen (step S32). A message "setting value will be overwritten. Continue restoration? Administrator authority is necessary for restoration", "Y (Yes)" button and "N (No)" button are contained in the screen. When the technician selects the "Y (Yes)" button on the screen, the CPU 56 proceeds the process to step S33, and when the technician selects "N (No)" button, the CPU 56 returns the process and returns the display to the menu screen W.

In step S33, the CPU 56 creates a temporary folder in the HDD 68 of the processing computer 50. In step S34, the CPU 56 decompresses the compressed setting value file stored in the FD 6 in the temporary folder, and performs the process of writing the decompressed setting value file to a predetermined directory of the processing computer 50 (step S35). In this case, "ipconfig.doc" (FIG. 15) recorded with OS information is not written, and is input by hand in the subsequent step. This is because the influence on the analyzing program that occurs when the setting value related to OS is automatically input is taken into consideration.

The CPU 56 then displays a message "input setting value of ipconfig.doc" in step S36, and the technician inputs the setting value recorded in "ipconfig.doc". In step S37, the CPU 56 checks whether or not the input of the setting value is completed, and deletes the temporary folder in step S38, returns the process, and returns the display to the menu screen W if completed. If the input is not completed, the process of S37 is again executed. In the present embodiment, a configuration of recording the setting value related to the communication of the OS in the ipconfig.doc, and in restoration, displaying the recorded setting value by opening the file of the ipconfig.doc, and manually inputting the setting value by the user is described, but is not limited thereto, and the setting value related to the communication of the OS may be automatically restored similar to the other setting values.

A "ipconfig help" button F7 is arranged on the menu screen W (FIG. 7), where when the technician selects the button F7 before or in the middle of the restoring process, the CPU 56 accepts the selection of the button F7 in step S7 of FIG. 6, and performs the process of step S8g. This process displays a method (instruction of input location and input procedure) of manually inputting "ipconfig.doc" on the display unit 54.

The setting value is restored in the processing computer 50, and a state of operating the analyzer 1 can be recovered through the above operations.

[Setting Value Clearing Process]

Figure 13:
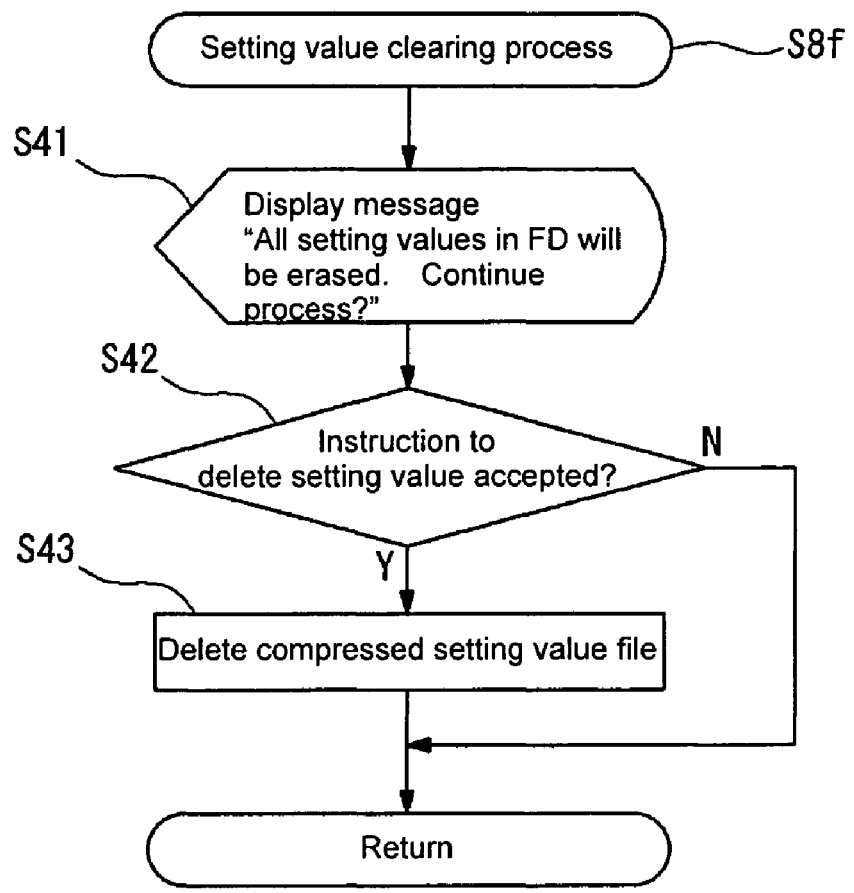
FIG. 13 is a flowchart showing a processing procedure of a setting value clearing process.

The backup program is executed in the processing computer 50 or the transmission/reception computer 5 and "setting value clear" button F6 is selected from the menu screen W when deleting the setting value in the FD 6 after acquiring the setting value of various programs from the processing computer 50 of the analyzer 1 and transmitting to the management device 2, or after restoring the setting value received from the management device 2 to the processing computer 50 of the analyzer 1. The CPU of the computer then accepts the selection of the button F6 in step S7 in FIG. 6, and performs the process of step S8f. FIG. 13 is a flowchart showing the process of step S8f, that is, the procedures of the setting value clearing process. In step S41, the CPU displays the screen for accepting the instruction for erasing the setting value on the display unit 54, and accepts the instruction to erase the setting value on the screen (step S42). A message "all setting values in the FD 6 will be erased. Continue the process?", "Y (Yes)" button, and "N (No)" button are contained in the screen. When the technician selects the "Y (Yes)" button in step S42, the process proceeds to step S43, and the CPU deletes the compressed setting value file stored in the FD 6, and thereafter returns the process and returns the display to the menu screen W. When the technician selects the "N (No)" button in step S42, the CPU returns the process, and returns the display to the menu screen W.

The FD 6 can then be used for acquisition and restoration of the setting value with respect to another analyzer, and transmission/reception of the setting value by deleting the compressed setting value file in the above manner.

[Configuration of Management Device 2]

The process performed in the management device 2 of the management center 4, that is, the process on reception, management, and transmission of the compressed setting value file will now be described. As shown in FIG. 1, the management device 2 is made up of one or a plurality of computers, and includes a database DB for storing specific information (model name and serial number) for specifying the analyzer 1, 100 and the setting information (compressed setting value file) of the analyzer in correspondence to each other with respect to the plurality of analyzers, 100 installed in the facilities 3 throughout the country. The management device 2 includes a reception means for receiving specific information and setting information transmitted from the transmission/reception computer 5, a registration means for registering the received specific information and setting information in the database, an accepting means for accepting the transmission of the specific information for specifying the setting information registered in the database from the transmission/reception computer 5, a transmission means for transmitting the setting information corresponding to the accepted specific information, and the like. The database DB is subjected to operation, maintenance, and management by the database management program.

Figure 16:
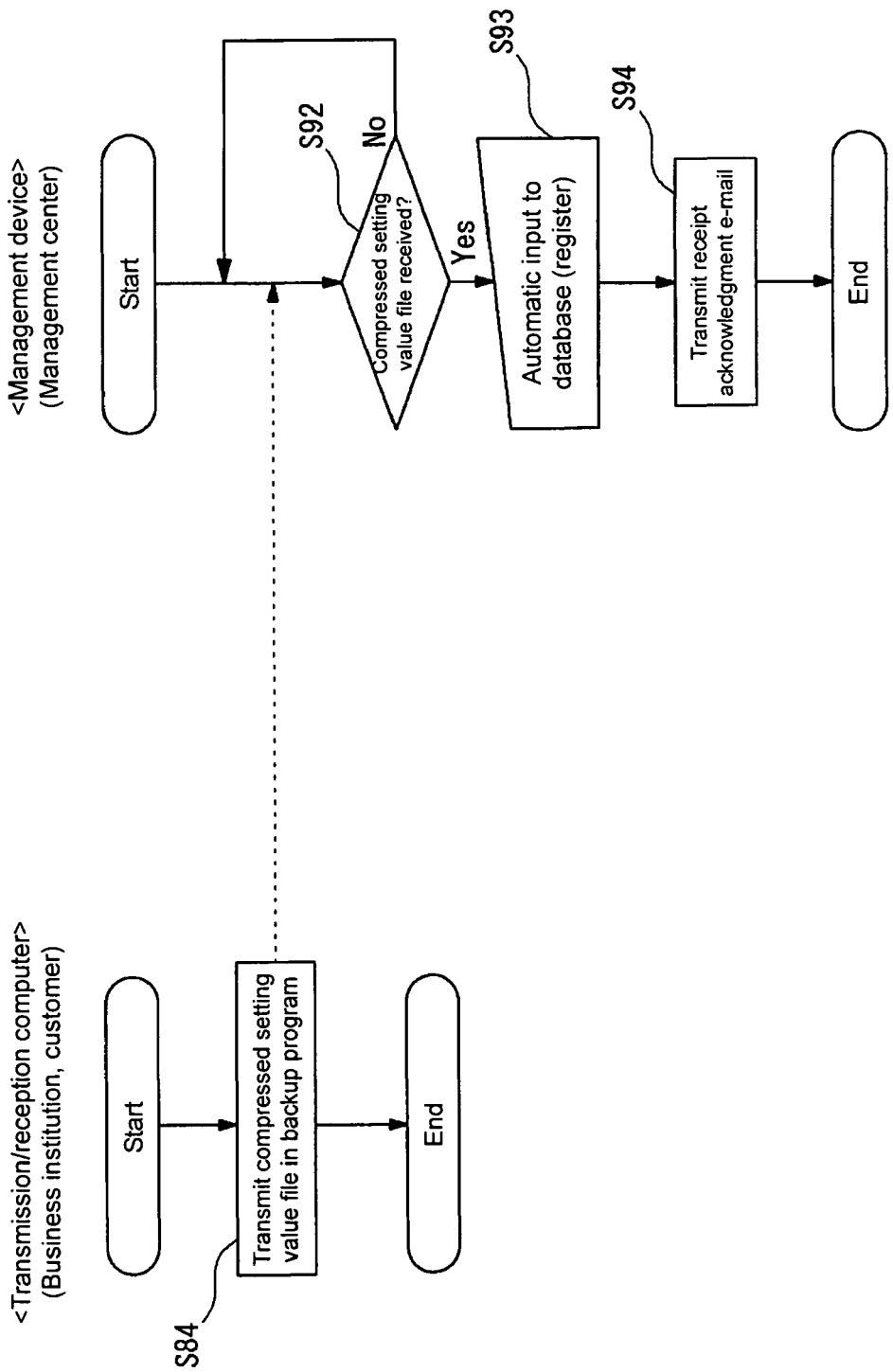
FIG. 16 is a flowchart showing a processing procedure from reception to registration of the compressed setting value file.

FIG. 16 is a flowchart showing a processing procedure of registering the specific information and the setting information received from the transmission/reception computer 5 to the database. Since the process of the transmission/reception computer 5 is described in detail in FIG. 10, the relevant process will be simplified in FIG. 16. In step S84, the transmission/reception computer 5 transmits an e-mail including the specific information and the compressed setting value file. The e-mail contains the specific information in the body text, and is attached with the compressed setting value file. The e-mail includes an e-mail address input to the input field C4 shown in FIG. 7. The management device 2 receives the e-mail in step S92. When receiving the e-mail including the specific information and the compressed setting value from the transmission/reception computer 5, the CPU of the management device 2 registers the specific information and the compressed setting value file in the database in step S93, and transmits an e-mail notifying reception to the transmission/reception computer 5 in step S94. The e-mail is transmitted to the e-mail address input to the input field C4. The technician can confirm that the specific information and the compressed setting value file are normally delivered to the management device 2 by the e-mail to the relevant e-mail address.

In step S93, registration of the specific information and the compressed setting value file to the database is not limited to being automatically performed, and when an e-mail attached with the compressed setting value file and containing the specific information in the e-mail body text or the title is transmitted from the transmission/reception computer, such e-mail may be received at the administrator (operator)'s computers of the management device, and the administrator may manually register the specific information and the compressed setting value file to the database. In this case, the computer for performing registration may be a different computer connected with the computer equipped with the database by means of a communication line.

Figure 18:
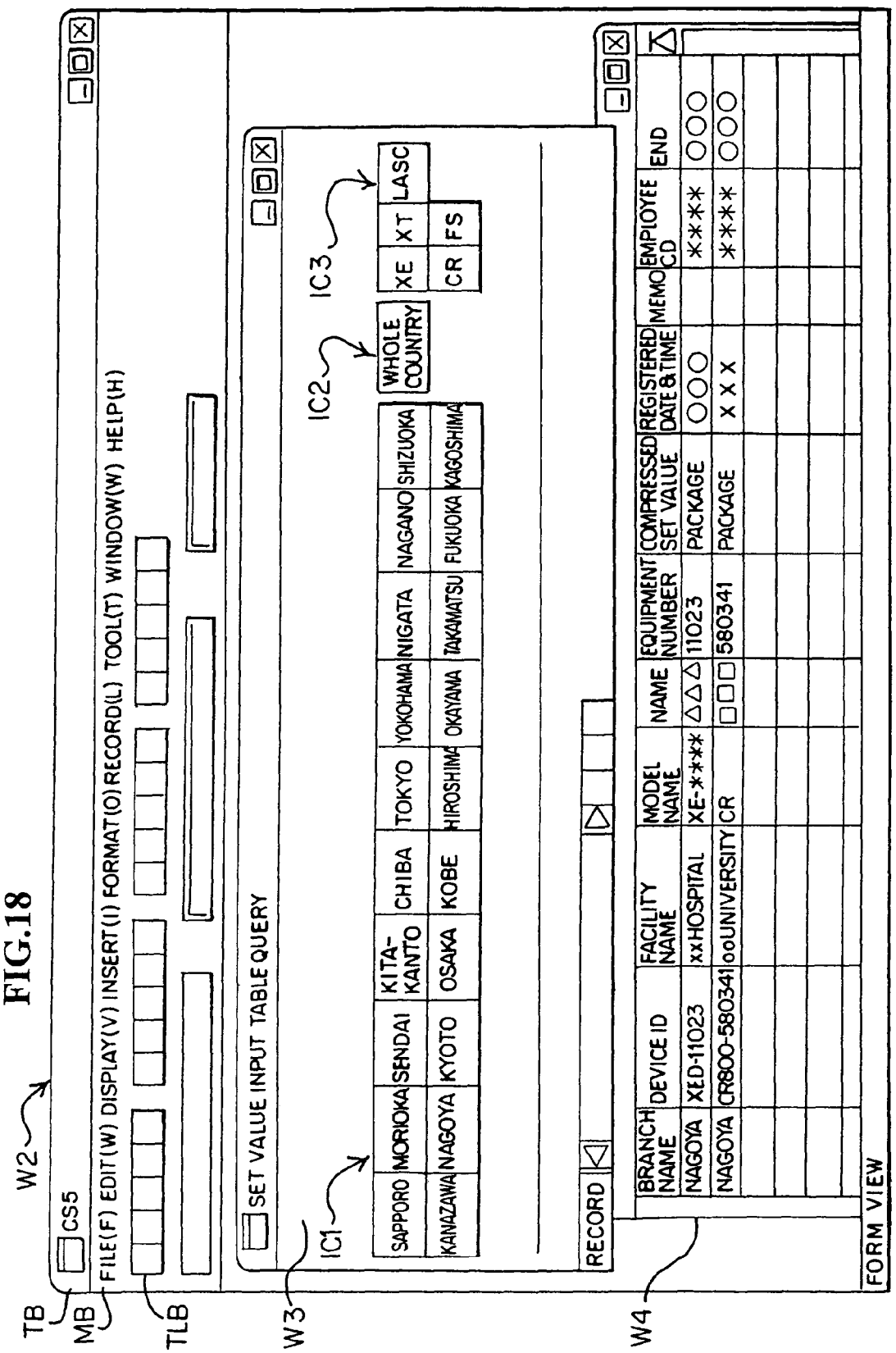
FIG. 18 is a view showing a display screen of the database software.

FIG. 18 is a display screen W2 displaying the registration content of the database by the management program. A title bar TB, a menu bar MB, and a tool bar TLB are arranged at the upper part of the display screen W2. In FIG. 17, a setting value input table query window (hereinafter referred to as query window) W3 displaying a plurality of search key icons IC1 to IC3, and a search result window W4 are displayed. A location IC1 and "whole country" IC2 of the facility 3, and a model name IC3 of the analyzer 1 are prepared for the search key icon of the query window W3. A search result of when the search key icon IC1 of "Nagoya" is selected for the location of the facility 3 is shown on the search result window W4.

Information registered in the database is displayed on the search result window W4 in a table form. Items of registration information are displayed on the first row, and the items include "branch name" or the name of the business institution 8, "device ID" of the analyzer, "facility name" at where the analyzer is installed, "model name" of the analyzer, "name" of the technician who transmitted the compressed setting value file, "equipment number" (serial number) of the analyzer, acquired "compressed setting value", "registered date and time", "MEMO", "employee CD (code number)" and "end" (name of contact person) of the contact person who input the information, and the like. Among them, the "device ID" is automatically generated from the registered information of the model name and the equipment number. The received compressed setting value file is attached to the "compressed setting value" field as a package. The management device 2 has a function serving as a WEB server, and the database can be browsed from the outside of the management device 2 through the WEB browser.

FIG. 17 is a flowchart showing a processing procedure of transmitting the setting information registered in the database DB of the management device 2 to the transmission/reception computer 5. The process of the transmission/reception computer 5 is shown in detail in FIG. 11, and thus will be simplified in FIG. 18. When the transmission/reception computer 5 transmits the specific information for specifying the setting information of the analyzer the computer desires to receive in step S65, the management device 2 receives the specific information in step S95. In step S96, the CPU of the management device 2 searches for the setting information corresponding to the accepted specific information from the database, and transmits the setting information to the transmission/reception computer 5 in step S97. When the CPU of the transmission/reception computer 5 receives the setting information transmitted from the management device 2 in step S67, the process terminates.

The embodiment described in detail above has the following advantages.

(1) The setting information management system of the present embodiment acquires the setting information for a plurality of types of analyzers 1, 100 by using the backup program, and thus does not need to create the backup program for every type of analyzer 1, 100. Therefore, the cost and the man hour necessary for creating the program can be reduced.

(2) The information management system of the present embodiment acquires the setting information for a plurality of types of analyzers 1, 100 by using the backup program, and manages the setting information by the management device 2, and thus the setting information for a plurality of types of analyzers can be collectively managed, whereby the user does not need to manage the setting information for every analyzer, and the load of the user can be alleviated. By having the service provider (analyzer manufacturing company) that performs the maintenance service of the analyzer hold the management device, the user does not need to manage the setting information, the service provider does not need to manage the setting information for every analyzer, and the setting information can be easily managed.

(3) In the setting information management system of present embodiment, the backup program is stored in the FD 6, and thus when the FD 6 is attached to the processing computer 50 of the analyzer 1, the backup program can be executed on the processing computer 50, and acquisition and restoration of the setting information can be easily performed. Therefore, the backup program does not need to installed in the processing computer 50 in advance.

(4) The backup program can function the computer as the transmission means for transmitting the setting information to the management device 2 and the reception means for receiving the setting information from the management device 2, and thus the transmission/reception program does not need to be installed in advance in the computer used in transmission/reception. Therefore, the transmission/reception of the setting value can be performed from any computer as long as the connection is established with the management device 2 by means of the network 7.

(5) The backup program functions the processing computer 50 to acquire and restore the setting value of the analyzing program for controlling the analyzer 1, 100 and the setting value of the other related programs (OS and auxiliary program), and thus the setting value of the related program other than the analyzing program can be simultaneously restored when initializing or replacing the processing computer 50.

(6) The backup program functions the processing computer 50 to acquire and restore the setting value for communication such as IP address, and thus a state of communicating the processing computer 50 with the outside by restoring the setting value.

(7) The backup program is configured to respond to the plurality of types of analyzers 1, 100, and thus acquisition and restoration of the setting information can be performed with the same operation with respect to different models, and the operation load of the technician can be alleviated.

The present invention is not limited to the embodiment, and can be appropriately design changed. For instance, the present invention may be performed in the following manner.

(1) In the embodiment, the FD 6 is used for the removable storage medium 6, but is not limited thereto, and may be optical disc such as MO, CD-R etc., flash memory such as USB memory etc., HDD of portable type, and the like. However, the generally used FD 6 is preferably used as the storage medium 6 in order to be responded to the plurality of new and old analyzers 1, 100 as in the present embodiment.

(2) Not only the backup program, but also a DOS (Disc Operating System) executable from the storage medium 6 may be stored in the storage medium 6. In this case, the setting value can be acquired as an emergency measure by executing the backup program with the DOS activated even if the OS of the processing computer 50 is not activated.

(3) A method of receiving the setting information from the database DB of the management device 2 may include browsing the content of the database from an external computer by the WEB browser etc., and downloads the setting information from the display screen of the WEB browser.

The invention claimed is:

1. A setting information management system comprising:
   a plurality of types of analyzers comprising a measurement unit for measuring a sample and outputting measurement result data, and a processing computer for processing the measurement result data output from the measurement unit; and
   a computer readable portable storage medium storing a backup program; wherein
   the backup program is configured to cause the processing computer to function as,
   determining means for determining the type of the analyzer when the backup program is executed by the processing computer of the analyzer,
   setting information acquiring means for acquiring setting information of a program introduced to the processing computer of the analyzer from the processing computer based on a determination result of the determining means, and
   storage means for storing the setting information acquired by the setting information acquiring means in the storage medium.

2. The setting information management system according to claim 1, further comprising a setting information management device for storing the setting information acquired from the plurality of types of analyzers.

3. The setting information management system according to claim 2, wherein
   the backup program is configured to cause a computer to function as transmission means for transmitting the setting information stored in the storage medium; and
   the setting information management device comprises storage means for storing the setting information transmitted by the transmission means.

4. The setting information management system according to claim 2, wherein
   the backup program is configured to cause a computer to function as
   accepting means for accepting input of specific information for specifying the setting information stored in the setting information management device, and
   specific information transmission means for transmitting the specific information accepted by the accepting means;
   the setting information management device includes,
   reception means for receiving the specific information transmitted by the specific information transmission means, and
   transmission means for transmitting the setting information specified by the specific information received by the reception means; and
   the backup program causes a computer to function as
   reception means for receiving the setting information transmitted from the setting information management device, and
   second storage means for storing the setting information received by the reception means in the storage medium.

5. The setting information management system according to claim 1, wherein the backup program is configured to cause the processing computer to function as restoration means for restoring the setting information stored in the storage medium in the processing computer.

6. The setting information management system according to claim 1, wherein the setting information acquiring means is configured to acquire setting information of an analyzing program for controlling the analyzer, and setting information of other related programs.

7. A setting information management system comprising:
   a plurality of analyzers comprising a measurement unit for measuring a sample and outputting measurement result data, and a processing computer for processing the measurement result data output from the measurement unit;
   a setting information management device for storing setting information of a program introduced to the processing computer of the analyzer; and
   a computer readable portable storage medium storing a backup program; wherein
   the backup program is configured to cause the processing computer to function as,
   setting information acquiring means for acquiring setting information of the program introduced to the processing computer in which the backup program is executed from the processing computer when the backup program is executed by the processing computer of the analyzer, and
   storage means for storing the setting information acquired by the setting information acquiring means in the storage medium; and
   the backup program is configured to cause a computer to function as transmission means for transmitting the setting information stored in the storage medium to the setting information management device.

8. The setting information management system according to claim 7, wherein the backup program is configured to cause a computer to function as
   specific information transmission means for transmitting specific information stored in the setting information management device;
   reception means for receiving the setting information specified by the specific information transmitted by the specific information transmission means from the setting information management device; and
   second storage means for storing the setting information received by the reception means in the storage medium.

9. The setting information management system according to claim 7, wherein the backup program is configured to cause the processing computer to function as restoration means for restoring the setting information stored in the storage medium in the processing computer.

10. The setting information management system according to claim 7, wherein the setting information acquiring means is configured to acquire setting information of an analyzing program for controlling the analyzer, and setting information of other related programs.

11. The setting information management system according to claim 10, wherein the setting information of related programs is setting information for communication for the processing computer to perform communication with the outside.

12. A setting information management device for managing setting information of a program introduced to an analyzer for analyzing a sample, the setting information management device comprising:
   a database for storing specific information for specifying an analyzer and setting information of a program introduced to the analyzer specified by the specific information in correspondence to each other for every plurality of analyzers;

reception means for receiving the specific information for specifying the analyzer and the setting information of a program introduced to the analyzer specified by the specific information from an external communication device; and registration means for registering the specific information and the setting information received by the reception means in the database.

13. The setting information management device according to claim 12, further comprising accepting means for accepting the specific information for specifying the setting information registered in the database from the external communication device, and a transmission means for transmitting the setting information corresponding to the accepted specific information to the communication device.

14. A setting information management method executed by a backup program stored in a portable storage medium by a processing computer of an analyzer; the method comprising the steps of:

determining a type of the analyzer in which the backup program is executed from a plurality of types of analyzers;

acquiring setting information of a program introduced to the processing computer based on the determination result; and storing the acquired setting information in the portable storage medium.

15. A computer program product storing a backup program executable by a plurality of analyzers, the computer program product comprising:

a portable storage medium; and instructions, on the portable storage medium, adapted to enable a general purpose computer to perform operations comprising:

step of acquiring setting information of a program introduced to a processing computer in which the backup program is executed from the processing computer when the backup program is executed by the processing computer of the analyzer;

step of storing the acquired setting information in the storage medium; and step of transmitting the setting information stored in the storage medium to the setting information management device when the backup program is executed by a computer communicably connected with the setting information management device storing the setting information.

16. The computer program product according to claim 15, wherein the instructions further includes a step of restoring the setting information stored in the storage medium in the processing computer of the plurality of analyzers.

17. The computer program product according to claim 15, wherein the setting information comprises a setting value of an analyzing program for analyzing a specimen.

18. The computer program product according to claim 15, wherein the step of acquiring the setting information comprises a step of acquiring setting information of an analyzing program for controlling the analyzer, and setting information of other related programs.

19. The computer program product according to claim 18, wherein the setting information of the related programs is setting information for communication for the processing computer to perform communication with the outside.

20. The computer program product according to claim 15, wherein the instructions further comprises a step of determining a type of the analyzer in which the backup program is executed from a plurality of types of analyzers.

* * * * *